US012722004B2

(12) United States Patent
Yoshida et al.

(10) Patent No.: US 12,722,004 B2
(45) Date of Patent: Sep. 1, 2026

(54) CURRENT STIMULATION APPARATUS

(71) Applicant: ITO CO., LTD., Tokyo (JP)

(72) Inventors: Daigo Yoshida, Tokyo (JP); Tsukasa Kurahashi, Tokyo (JP); Mayuko Kurahashi, Tokyo (JP); Fumihiko Sano, Tokyo (JP); Toshiki Hiroi, Tokyo (JP)

(73) Assignee: ITO CO., LTD., Tokyo (JP)

( * ) Notice: Subject to any disclaimer, the term of this patent is extended or adjusted under 35 U.S.C. 154(b) by 466 days.

(21) Appl. No.: 17/432,243

(22) PCT Filed: Feb. 27, 2020

(86) PCT No.: PCT/JP2020/008161
§ 371 (c)(1),
(2) Date: Aug. 19, 2021

(87) PCT Pub. No.: WO2020/175650
PCT Pub. Date: Sep. 3, 2020

(65) Prior Publication Data

US 2022/0184395 A1 Jun. 16, 2022

(30) Foreign Application Priority Data

Feb. 27, 2019 (JP) ................................ 2019-034960
Dec. 20, 2019 (JP) ................................ 2019-230731

(51) Int. Cl.
*A61N 1/36* (2006.01)
*A61N 1/04* (2006.01)

(52) U.S. Cl.
CPC ....... *A61N 1/36034* (2017.08); *A61N 1/0452* (2013.01); *A61N 1/0456* (2013.01); *A61N 1/0484* (2013.01); *A61N 1/36003* (2013.01)

(58) Field of Classification Search
CPC .............. A61N 1/36034; A61N 1/0452; A61N 1/0456; A61N 1/0484; A61N 1/36003;
(Continued)

(56) References Cited

U.S. PATENT DOCUMENTS

2011/0178571 A1* 7/2011 Tannebaum ....... A61N 1/36021 607/46
2013/0289667 A1* 10/2013 Wacnik .............. A61N 1/36171 607/2

(Continued)

FOREIGN PATENT DOCUMENTS

JP H08-112362 A 5/1996
JP 2001-333990 A 12/2001

(Continued)

OTHER PUBLICATIONS

European Patent Office, EP Search Report issued in EP patent application No. 20 762 949.4, Munich Germany, Oct. 19, 2022, 7 pages.

(Continued)

*Primary Examiner* — Benjamin J Klein
*Assistant Examiner* — Daniel Tehrani
(74) *Attorney, Agent, or Firm* — ASLAN LAW, P.C.

(57) ABSTRACT

A current stimulation apparatus that includes a waveform generator to output an electric signal; a control section to control the waveform generator; a set of electrodes to provide the output electric signal; and a power supply section to supply electric power to the waveform generator and the control section, where the electric signal is a fifth electric signal including: a first electric signal having an amplitude increasing from a first amplitude, the first amplitude being not zero; a second electric signal having a second amplitude and being output after the first electric signal; a third electric signal having an amplitude decreasing to a
(Continued)

third amplitude, the third electric signal being output after the second electric signal; and a fourth electric signal having a fourth amplitude, the fourth amplitude being not zero.

2 Claims, 36 Drawing Sheets

(58) Field of Classification Search
CPC .............. A61N 1/0551; A61N 1/36014; A61N 1/0492; A61N 1/36132; A61N 1/36021; A61N 1/36071; A61N 1/36146
See application file for complete search history.

(56) References Cited

U.S. PATENT DOCUMENTS

| | | | | |
|---|---|---|---|---|
| 2014/0031895 | A1* | 1/2014 | Rahimi | A61N 1/36021 607/46 |
| 2014/0067003 | A1 | 3/2014 | Vase et al. | |
| 2018/0133507 | A1* | 5/2018 | Malchano | G16H 40/63 |
| 2020/0206500 | A1 | 7/2020 | Kurahashi et al. | |

FOREIGN PATENT DOCUMENTS

| | | | | |
|---|---|---|---|---|
| JP | 2003-126272 | A | 5/2003 | |
| JP | 2003-339884 | A | 12/2003 | |
| JP | 2009213687 | A | 9/2009 | |
| JP | 2010-075401 | A | 4/2010 | |
| JP | 2010-094445 | A | 4/2010 | |
| WO | WO-2014021926 | A1 * | 2/2014 | A61B 5/0215 |
| WO | WO 2019/022127 | A1 | 1/2019 | |

OTHER PUBLICATIONS

VN Office Action issued in VN patent application No. 1-2021-05793, Ministry of Science and Technology, Socialist Republic of Vietnam, Nov. 17, 2023, 2 pages.

Japanese Patent Office, JP Office Action issued in JP patent application No. 2021-502383, Japan, Feb. 21, 2023, 4 pages.

Japanese Patent Office, JP Office Action issued in JP patent application No. 2021- 502383, Japan, May 16, 2023, 5 pages.

Japanese Patent Office, JP Office Action issued in JP patent application No. 2021-502383, Japan, Dec. 6, 2022, 4 pages.

CN Office Action issued in CN patent application No. 202080017311.2, The State Intellectual Property Office of People's Republic of China, China, Feb. 23, 2024, 3 pages.

VN Office Action issued in VN patent application No. 1-2021-05793, Intellectual Property Office of Vietnam (VN), May 16, 2025, 1 page.

* cited by examiner

CURRENT STIMULATION APPARATUS

CROSS-REFERENCE TO RELATED APPLICATIONS

This application claims priority to JP Patent Application No. 2019-034960 filed on Feb. 27, 2019 and to JP Patent Application No. 2019-230731 filed on Dec. 20, 2019, and this application claims priority to and is a 371 of international PCT Application No. PCT/JP2020/008161 filed on Feb. 27, 2020, the entire contents of which are hereby incorporated by reference.

TECHNICAL FIELD

The present invention relates to a current stimulation apparatus for use in percutaneous electric stimulation, such as in therapy, rehabilitation, testing, massaging, physical condition management, fatigue recovery, injury prevention, post exercise body care for muscles and joints or beauty care and so on.

BACKGROUND OF ART

A so-called physical therapy by which treatment, massage, diagnosis, training, or cosmetic treatment is performed by applying physical energy from outside to necessary parts such as affected parts, has been attracting attention, such as treatment using electromagnetic waves such as very high frequency waves or microwaves, treatment using low frequency or high frequency currents, electric potential therapy, treatment by microcurrent, treatment by ultrasonic waves, or the like, and many medical devices, diagnostic devices, training devices, and cosmetic devices for realizing these therapies have been put into practical use. In this specification, a physical energy used for treatment, cosmetic treatment, or diagnosis, for example, a current or a voltage having an AC component or a frequency component such as a low frequency or a high frequency, or a sine wave, a pulse, or an impulse are collectively or respectively referred to as an electric signal or a pulse; and may, in some cases, also be referred to as a therapeutic wave, an electric stimulation, or an electric signal. Furthermore, the electric signal or pulse may be a pulse train by a rectangular pulse or a pulse train by a composite pulse; and may, in some cases, also be a sine wave, a triangle wave, a sawtooth wave, or an impulse train. In addition, a composite wave produced by the interaction of multiple pulses is simply referred to as an electric signal or pulse, and a composite wave produced by a sine wave is simply referred to as an electric signal or pulse.

Hereinafter in this specification, a treatment device, a medical device, a massage machine, a diagnostic device, a training device, a device used for physical condition management, fatigue recovery, or the like, and a cosmetic device using electric stimulation are collectively referred to as a current stimulation apparatus. Each of percutaneous electric stimulation procedures, such as treatment, diagnosis, massage, physical condition management, or treatment with cosmetic device, performed by using a current stimulation apparatus, electric stimulation is respectively or collectively referred to as treatment. A person who uses a current stimulation apparatus, such as a person who uses a current stimulation apparatus to perform a treatment or a massage, a person who performs a diagnosis using a current stimulation apparatus, or a person who performs a cosmetic treatment using a current stimulation apparatus, is referred to as a user; whereas a treated person is referred to as a patient. Further, a region of the human body to which electric stimulation is applied or which is treated is referred to as an affected part. Therefore, unless expressly stated otherwise, the description of current stimulation apparatuses does not exclude massagers, diagnostic or cosmetic device, or equipment for preventing injuries, and even the description of a patient does not only mean an injured or ill person, but includes a person undergoing an examination or a cosmetic procedure. Likewise, the term "affected part" does not only mean an injured or affected part, but also a part of the body to be examined or a part of the body to be cosmetically treated. Thus, electric signals used in therapy do not exclude electric signals or pulses used for massage, diagnosis, physical condition management, or cosmetic purposes, unless otherwise specified.

Currently, current stimulation apparatuses that have two or three pairs of electrodes, i.e., four or six electrodes have been put into practical use in which electric signals of different frequencies are supplied to the affected part from each pair of electrodes provided so as to surround the affected part, and an interference wave is generated in the body to perform a treatment. In the treatment using the interference wave, there is an advantage that effective treatment can be performed even if the affected part is at a position deeper than the body surface.

The Prior Art Literature

Patent Literature

Patent Document 1: JP H08-112362

DISCLOSURE OF THE INVENTION

Problems to be Solved by the Invention

The electric signal supplied to the affected part reaches deeper as the frequency increases. However, at higher frequencies, given muscle contraction occurs, for example; but as a matter of course, effects due to low-frequency electric signals, for example, massage effects, are less likely to be obtained. In techniques such as those described in above-noted patent document 1, by supplying electric signals of different frequencies, electrical interference can be generated to supply both low-frequency and high-frequency effects to the affected part. However, at least two, e.g. three, pairs of electrodes, i.e. four or more, e.g. six electrodes, are required as electrodes in order to supply different electric signals separately to the affected part. In such a configuration in which a large number of electrodes are used in this manner, no aimed effect or sufficient therapeutic efficiency is obtained unless the electrodes are correctly arranged in a predetermined order at predetermined positions. In addition, if the electrode used is a consumable such as an adhesive pad, the running cost for the treatment may need to be twice or more, for example three times, and high treatment costs may be required. It is an object of the present invention to solve these problems and to provide a current stimulation apparatus with high therapeutic efficiency.

Means for Solving the Problem

In order to achieve the above problem solution, the present invention has the following means. That is, the current stimulation apparatus includes: a waveform generator to output an electric signal; a control section to control the waveform generator; a set of electrodes to provide the output electric signal; and a power supply section to supply electric power to the waveform generator and the control section, where the electric signal is a fifth electric signal including: a first electric signal having an amplitude increasing from a first amplitude, the first amplitude being not zero; a second electric signal having a second amplitude and being output after the first electric signal; a third electric signal having an amplitude decreasing to a third amplitude, the third electric signal being output after the second electric signal; and a fourth electric signal having a fourth amplitude, the fourth amplitude being not zero.

Further, the current stimulating apparatus of the present invention is characterized in that the fifth electric signal is repeatedly output at different times.

Effects of the Invention

The present invention can provide a physical therapy that generates multiple effects at a time, and can improve the efficiency of treatment because treatment as much as or more than interference wave treatment which uses two or more pairs of electrodes with one pair of electrodes. Furthermore, since only one pair of electrodes are used, there is no incorrect arrangement or order of the electrodes, and no decrease in treatment efficiency due to misplacement of the electrodes is induced. Furthermore, since less familiar treatment can be performed, a current stimulation apparatus, with which high treatment efficiency can be maintained, can be provided.

DETAILED DESCRIPTION OF THE EMBODIMENTS

First Embodiment

Figure 1:
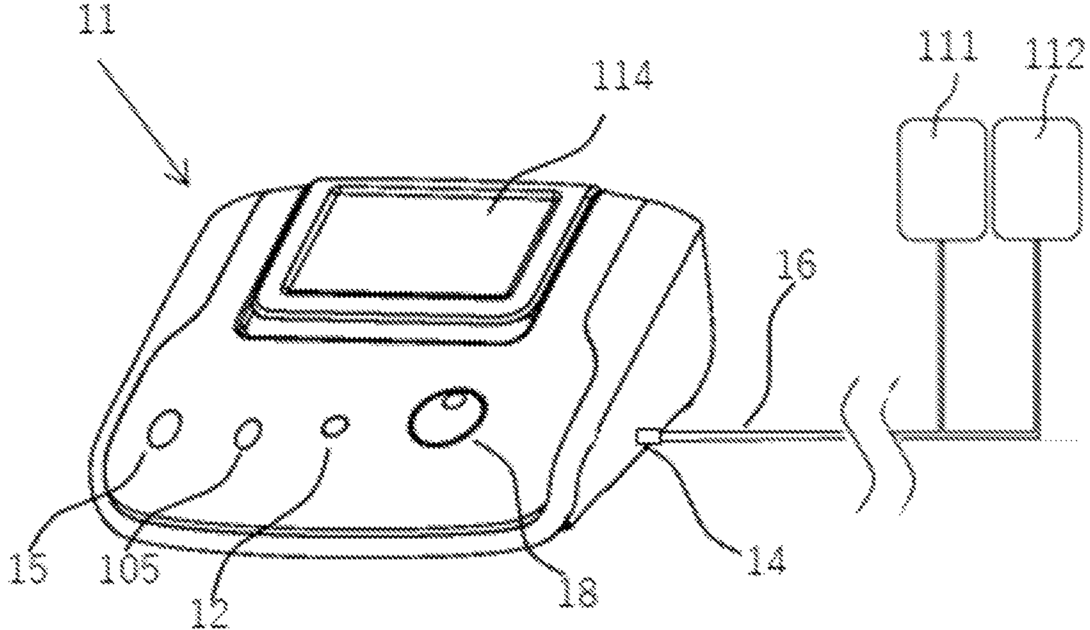
FIG. 1 is an explanatory diagram for explaining the description of the main body of the current stimulation apparatus of the present invention.

Next, the electric signal according to the present invention and the apparatus for outputting the electric signal according to the present invention will be described together with the treatment method according to the present invention. FIG. 1 is a perspective view of a main body section 11 of a current stimulation apparatus 1 used in the present embodiment for explaining the present invention. A main power 15, an encoder 18, a display section 114, a switch 105, a stop switch 12, a connector section 14, etc. are provided on the front of the main body section 11 of the current stimulation apparatus 1, and an electrode pad A111 and the electrode pad B112 are connected to the connector section 14 by a cord 16.

In the treatment, the electrode pad A111 and the electrode pad B112, which are a pair of conductive adhesive pads, are directly attached to the skin of the affected part or the vicinity of the affected part, for example, so as to sandwich the affected part, and electric signals are supplied to the affected part by the current flowing from the electrode pad A111 to the electrode pad B112 or from the electrode pad B112 to the electrode pad A111.

Instead of the electrode pad A111 or the electrode pad B112, for example, a suction cup separately connected to a suction device may be used as the electrode to be used, and electric signals may be supplied to the affected part using an electrode disposed in the suction cup. A conductive member that is conductive but not tacky, for example, conductive rubber or the like may be used, instead of a conductive adhesive pad. In the case where the member does not have such an adhesive property, a belt (not shown) may be separately used to fix them.

Figure 2:
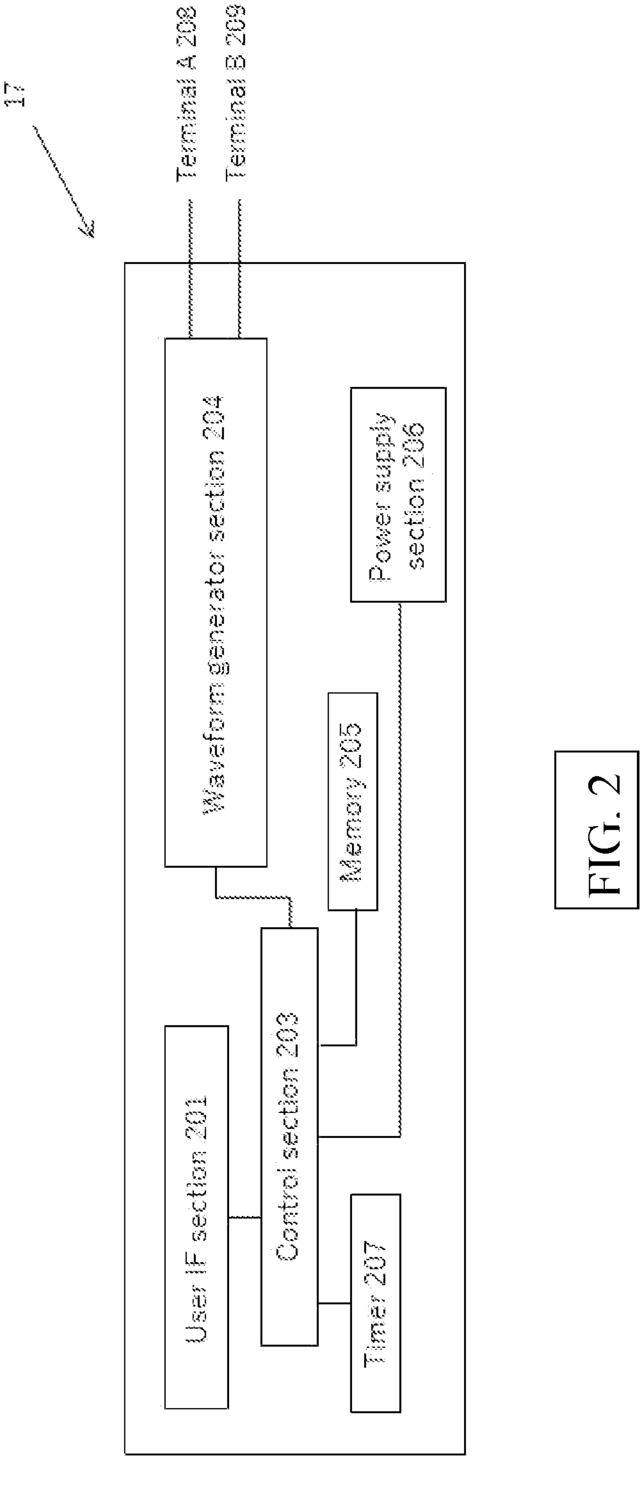
FIG. 2 is an explanatory diagram for explaining a control device of the current stimulation apparatus of the present invention.

FIG. 2 shows a block diagram of a controller 17. The controller 17 is disposed in the main body section 11 to control the operation of the main body section 11. The controller 17 comprises a waveform generator section 204 as an output circuit for outputting the electric signals, a control section 203 to control the waveform generator section 204, a timer 207, a user IF section 201, a power supply section 206, and a memory 205, etc. The control section 203 has a built-in interface section connected to each section in addition to CPU and the internal memory, and is connected to control the waveform generator section 204 for generating electric signals for providing current stimulation, the timer 207 for managing the output for a certain period of time, the user IF section 201 connected to the switch 105 and the display section 114, and the memory 205. Power to be consumed in each section is controlled to a predetermined constant voltage value by the power supply section 206 and is supplied to each section through the control section 203.

The current stimulation apparatus 1 is used as follows. First of all, the electrode pad A111 and the electrode pad B112 are attached to the affected part by the user, and then the main power 15 is turned on. When the main power 15 is turned on, buttons, and the like, e.g., buttons for a treatment mode or an output level, which are interfaces for the status and various settings of the main body section 11, are displayed on the display section 114, for example. The display section 114 is a thin display such as a liquid crystal display of a touch panel type and also serves as a display means and an input means. The displayed output level is tapped to enable the encoder 18, and by rotating the encoder 18, an amplitude, which is an output of an electric signal described later, can be set. When the user further selects the desired treatment mode using the display section 114 the parameters of the electric signals used in the selected treatment mode are read from the memory 205 and supplied to the waveform generator section 204, and when the user subsequently presses the switch 105, the information is provided via the user IF section 201 to the control section 203, and the control section 203 instructs the waveform generator section 204 to output an electric signal as described later. The waveform generator section 204 outputs electric signals according to the supplied parameter, and the output electric signal is supplied to the electrode pad A111 via the connector section 14 connected to a terminal A208 and the cord 16, and to the electrode pad B112 via the connector section 14 connected to a terminal B209 and the cord 16. At the same time, the information is sent to the timer 207, and the timer 207 starts to measure the time, e.g. treatment time, for outputting the electric signal by the waveform generator section 204, that is, 20 minutes for which the electric signal is supplied to the affected part. The information on the measurement by the timer 207, e.g. the information that a predetermined time has elapsed is fed back to the control section 203. In response to the feedback information, the control section 203 stops supplying power to the waveform generator section 204, and as a result, the output of the electric signal is stopped. The treatment time is not limited to 20 minutes, and may be equal to or more than 20 minutes, or less than 20 minutes, or may be to allow the user to set or adjust considering the condition of the affected part as necessary. It should be noted that the stop switch 12 is used to forcibly stop the output of all electric signals in the event of an accident.

The control section 203 instructs the user IF section 201 to indicate that an electric signal is being output in accordance with the power supply to the waveform generator section 204 and the user IF section 201 displays the letter "ON" showing that an electric signal is output, on the display section 114. In addition, if the control section 203 stops outputting an electric signal, the control section 203 transmits predetermined information to the user IF section 201, and the user IF section 201 instructs the display section 114 to display "OFF" instead of "ON" according to the information.

Figure 3A:
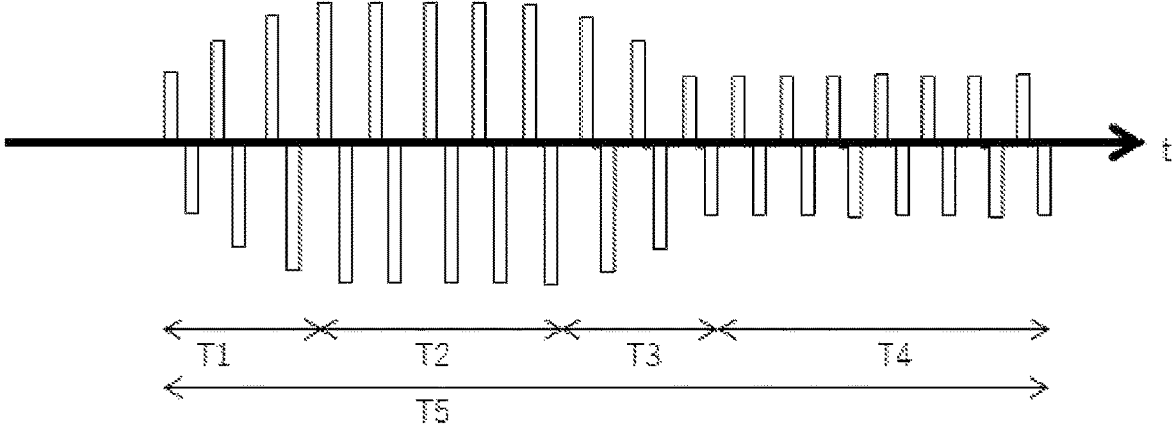
FIG. 3A is an explanatory view for explaining an electric signal for use in the current stimulation apparatus of the present invention.

FIG. 3A schematically illustrates electric signals supplied to a human body, e.g., an affected part, in accordance with the present invention. The horizontal axis indicates time, the vertical axis indicates amplitude, such as an amplitude of a current. If a collection of pulses is referred to as a pulse group, the electric signal in FIG. 3A is composed of a plurality of pulse groups. In particular, the electric signal in FIG. 3A is expressed as the fifth electric signal comprising the first electric signal, which is a group of pulses whose amplitude increases from the first amplitude that is not at zero to the fifth amplitude, the second electric signal, which is a group of pulses whose amplitude is the second amplitude that is not at zero, and output following the first electric signal, the third electric signal, which is a group of pulses, whose amplitude decreases from the sixth amplitude to the third amplitude, and output following the second electric signal, and the fourth electric signal, whose amplitude is the fourth amplitude that is not at zero. For example, the time at which the first electric signal, the second electric signal, the third electric signal, and the fourth electric signal, are output, may be 1 second, 0.8 second, 1 second, and 0.8 second, respectively. FIG. 3A shows the vertical axis as the current value, but the vertical axis may be shown as the voltage value, for the electric signal. For example, the first amplitude, the second amplitude, and the third amplitude may be 14 mA, 17 mA, 14 mA, respectively, which cause slight muscle contractions and may be used to ameliorate pain or recover from fatigues.

Figure 3B:
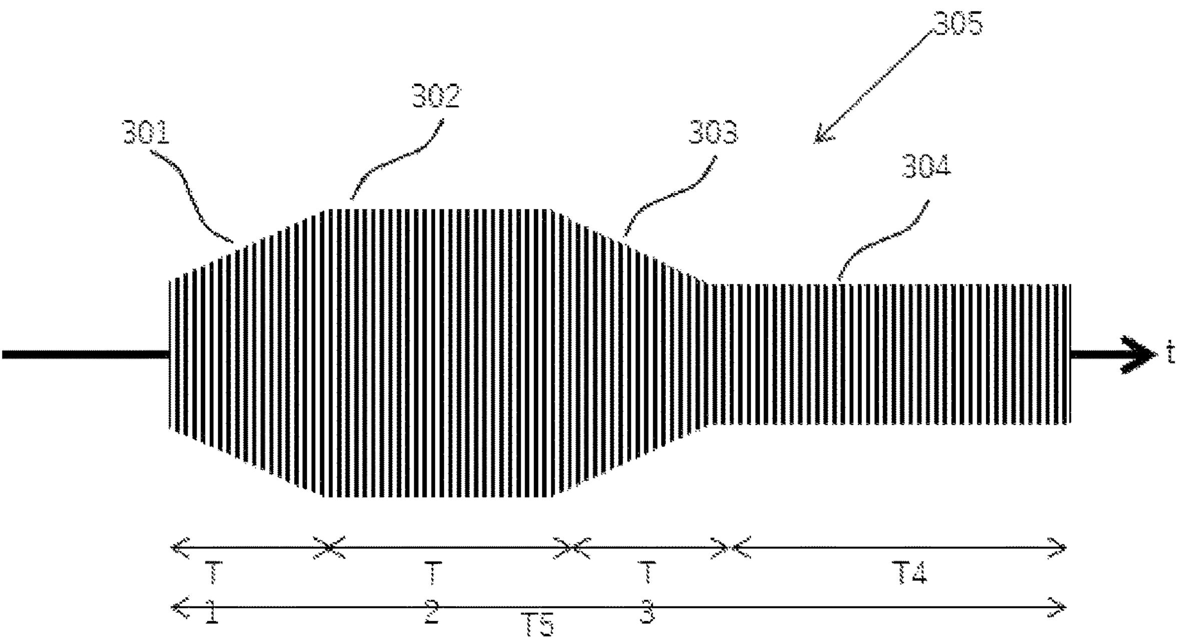
FIG. 3B is an explanatory view for explaining an electric signal for use in the current stimulation apparatus of the present invention.
Figure 3C:
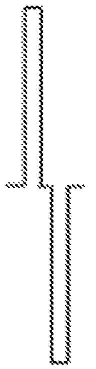
FIG. 3C is an explanatory view for explaining an electric signal for use in the current stimulation apparatus of the present invention.

FIG. 3B is a schematic representation of the fifth electric signal, and in the following description, schematic diagrams as shown in FIG. 3B will be used for explanation for simplification. The first electric signal, the second electric signal, the third electric signal, the fourth electric signal, and the fifth electric signal are respectively shown as the first electric signal 301, the second electric signal 302, the third electric signal 303, the fourth electric signal 304, and the fifth electric signal 305 in FIG. 3B. In FIG. 3A, each electric signal is repeatedly used with the pulse waveform as shown in FIG. 3C as one cycle of the basic pulse and by being controlled to change the amplitude of the basic pulse (hereinafter referred to as variable control), whereby the first electric signal 301, the second electric signal 302, the third electric signal 303, the fourth electric signal 304, and the fifth electric signal 305 are configured. In the following description, the first electric signal 301, the second electric signal 302, the third electric signal 303, the fourth electric signal 304, and the fifth electric signal 305 are simply referred to the first signal, the second signal, the third signal, the fourth signal and the fifth signal. Since the second signal and the fourth signal, which are the high frequency signals, are alternately applied by the fifth signal, the effect of the low frequency can be obtained even in the deep portion, and the treatment effect of both the high frequency and the low frequency can be applied to the patient at a time to improve the treatment efficiency. The treatment method using such an electric signal is extremely effective and can improve the treatment efficiency. Further, the second signal and the fourth signal may have the same frequency or different frequencies.

Figure 3D:
FIG. 3D is an explanatory view for explaining an electric signal for use in the current stimulation apparatus of the present invention.

The basic pulse is not limited to this, and the first signal, the second signal, the third signal, the fourth signal, and the fifth signal may be configured by repeatedly using the electric signals with a pulse waveform as shown in FIG. 3D as the basic pulse while variably controlling the amplitude of the basic pulse. Alternatively, the fifth signal may be configured by using at least one of the pulse waveform of FIG. 3C and the pulse waveform of FIG. 3D as a basic pulse or by mixing both of them in the basic pulse. The basic pulse may be a sine wave, a triangle wave, a sawtooth wave, an impulse train, or a composite waveform thereof, instead of a rectangular pulse. Although the exemplified pulse waveform has a basic pulse such that the positive and negative amplitudes are equal, but pulse waveform not limited thereto, and may be a pulse waveform such that the positive and negative amplitudes are different or that pulses having equal positive and negative amplitudes are offset. The pulse of 100 μsec at 300 Hz can be used as the basic pulse, but the basic pulse is not limited to this, and medium frequency or high frequency, such as 500 Hz or 800 Hz, which is equal to or more than 10 times the fifth signal, may be used. In FIGS. 3A and 3B, an example in which the first amplitude, the third amplitude, and the fourth amplitude are the same is shown, but the present invention is not limited to this, and at least one of them may have an amplitude different from the others. Similarly, FIG. 3A and FIG. 3B show examples in which the fifth amplitude and the second amplitude are the same, and the second amplitude and the sixth amplitude are the same. But not limited thereto, the fifth amplitude may be different from the second amplitude, and the second amplitude may be different from the sixth amplitude.

Figure 4:
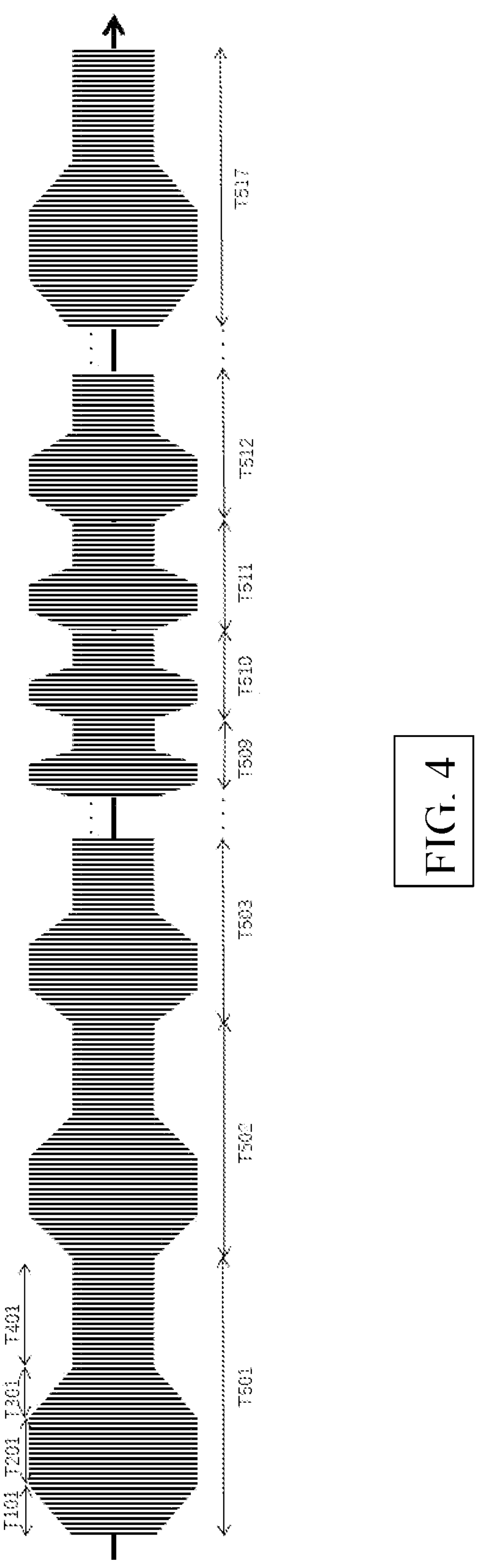
FIG. 4 is an explanatory view for explaining an electric signal for use in the current stimulation apparatus of the present invention

FIG. 4 shows another example of the electric signal supplied to the affected part and the fifth signal is repeatedly output in different periods of time. When the treatment is started, the fifth signal is output at T501, and at T502, T503 . . . , respectively. When the time from the start of the first signal to the start of the next first signal like T501, T502, T503 . . . is referred to the duration of the fifth signal, or simply the duration, the duration of the fifth signal is 1 second in T501, 0.67 second in T502, 0.5 second in T503, 0.4 second in T504, . . . , and 0.2 second in T509, becoming successively shorter. Thereafter, the duration of the fifth signal is sequentially lengthened such that 0.22 second in T510, 0.25 second in T511, 0.29 second in T512, . . . , and is controlled to finally return to 1 second in T517. Thereafter, such control is repeated. For example, T517 is followed by T518 and the fifth signal of 0.67 second is output, i.e., in the duration from T501 to T517 during the treatment period, the fifth signal is output repeatedly while gradually changing the duration time.

In the control as shown in FIG. 4, since the duration of the supplied electric signal is not constant but is always variably controlled, and the patient feels that the frequency of the supplied electric signal has changed. Therefore, unlike in the case where only the electric signal having a constant frequency is repeatedly supplied, the effect of a favorable electric stimulation, which is difficult to be used to the electric stimulation, continues for a long period of time, and the therapeutic effect can be increased.

In the control as shown in FIG. 4, if T501, etc. is considered to be one cycle, since the fifth signal is 1 second in T501, the frequency of the fifth signal is 1 Hz in T501, and since the fifth signal is 0.2 second in T509, the frequency becomes several 5 Hz. As a result, the frequency is controlled to vary from 1 Hz to 5 Hz. But not limited to this, the frequency may be controlled from 2 Hz or may be controlled up to 10 Hz. Further, in the control of FIG. 4, the frequency is controlled from 1 Hz to 5 Hz at a constant rate of change of 0.5 Hz, but a control at a constant rate of change of, for example, 0.4 Hz or 0.6 Hz, or of 1 Hz. FIG. 4 shows that the frequency is changed from 1 Hz to 5 Hz, followed by control to change from 5 Hz to 1 Hz, after which this control of frequency is repeated.

The frequency may be controlled at a constant rate. For example, the frequency changes at a constant rate, such as 1 Hz for T501, 1.5 Hz for T502, 2.2 Hz for T503, 3.3 Hz for T504, and 5 Hz for T505. For example, the frequency may be controlled to increase by 1.5 times or decrease by ⅓. Further, a configuration may be adopted in which the change of the frequency is controlled by applying a specific mathematical expression. In FIG. 4, the frequency of the fifth signal is changed from 1 Hz to 5 Hz, but not limited to this, for example, the frequency may be controlled to increase from the fifth signal, whose duration is 1 second or more, such as 0.1 Hz or 0.5 Hz, and the frequency of the fifth signal may be controlled by the variable control, so that the duration is 1 second or less, that is, so that the frequency of the fifth signal is controlled from 1 Hz or less to 1 Hz or more. Alternatively, for example, the frequency may be controlled so that the duration of the fifth signal may be constantly 1 second or more, that is, 1 Hz or less, or may be controlled to be constantly 1 second or less, that is, 1 Hz or more.

Here, for T1 to T5, T1 is for the duration of the first signal, T2 for the duration of the second signal, T3 for the duration of the third signal, T4 for the duration of the fourth signal, and T5 for the duration of the fifth signal. Further, in the case of T501, with the subscript 01, T101 is indicated as the duration of the first signal, T201 for the duration of the second signal, T301 for the duration of the third signal, and T401 for the duration of the fourth signal, and these are indicated using the fifth signal at the T501 as the example in the FIG. 4. Thereafter, using 02 in T502, T102, T202, T302, and T402 are denoted, and using 03 in T503, T103, T203, T303, and T403 are denoted, and the same thing will be applied thereafter.

The control shown in FIG. 4 is the control such that the duration of each signal constituting the fifth signal gradually becomes shorter or gradually becomes longer. Therefore, at least one of T1, T2, T3, and T4 is controlled to become shorter or longer as T5 changes. For example, if T1 is 30% of T5, T25 is 14% of T5, T3 is 30% of T5, and T4 is 26% of T5, T501 is 1 second, T101=is 0.3 second, T201 is 0.14 second, T301 is 0.3 second, and T401 is 0.26 second in the example of this embodiment. In T503, T503 is 0.45 second; and therefore each of T1 to T4 in T503 may be 45% of each value in T501. T505 is 0.33 second; and therefore in T505, 33% of these signals at T101, T201, T301, and T401 may be determined as T105, T205, T305, and T405 respectively.

The duration of each signal of the fifth signal may be controlled not by increasing or decreasing each of the duration of each signal at a constant rate, as in the control in FIG. 4, but so that the amount of change of some signal, for example, the first signal only, or the first signal and the third signal, is larger than the amount of change of the second signal. In this case, the first signal or the third signal greatly increases or decreases. However, the second signal increases or decreases less than the first signal or the third signal. In addition, the increase or decrease of the duration of the fourth signal may also be controlled to be small, which is suitable for use with more emphasis on the effect of the second signal.

On the other hand, if a pain due to current stimulation is likely when the first signal or the third signal becomes too short, the duration of the first signal or the third signal may be controlled so that the increase or decrease thereof is less than the duration of the second signal, although the duration of the second signal is increased or decreased greatly. The first signal and the third signal have an effect of relieving the pain caused by the current stimulation, and are suitable for the case where emphasis on the effect of the first signal or the third signal is desirable.

The control in which the increase or decrease of the first signal or the third signal is reversed may be applied to the second signal. For example, the control may be applied such that T101, T102, T103, . . . T109 are sequentially shorter such as 0.33 second, 0.22 second, 0.17 second, 0.13 second, 0.11 second, 0.095 second, 0.083 second, 0.074 second, 0.067 second; and on the other hand, T201, T202, T203, . . . , T209 are sequentially longer such as 0.005 second, 0.01 second, 0.015 second, 0.02 second, 0.025 second, 0.03 second, 0.035 second, 0.04 second, 0.045 second. Assuming that the durations of the first and third signals are equal, then the durations of the fourth signals, that is, T401, T402, and T403, . . . , T409 are 0.33 second, 0.21 second, 0.15 second, 0.11 second, 0.086 second, 0.065 second, 0.048 second, 0.034 second, 0.022 second. Such a control is suitable for a case where the effect of the second signal is desired to be emphasized in use; for example, for a case where, even when the duration of the fifth signal is shortened, a stronger user experience is desirable. The duration of each signal may be calculated by a mathematical expression such that desired control becomes possible. For example, in the above control, the duration of the second signal (T201, T202, T203, . . . T209) may be calculated by substituting each value of 1 second, 0.67 second, 0.5 second, . . . 0.2 second as the duration of the fifth signal T501, T502, T503, . . . T509, to, for example, T of 0.01/T−0.005. The duration of the first signal (T101, T102, and T103, . . . T109) may be calculated by substituting the duration of the fifth signal, T501, T502, T503, . . . T509, to T of T/3. The duration of the third signal is assumed to be equal to that of the first signal. The duration of the fourth signal, T401, T402, T403, . . . T409 may be calculated as the value obtained by subtracting the duration of the first signal, the second signal, and the third signal from the duration of the fifth signal T501, T502, T503, . . . T509. Note that in the examples given here, the duration of the first signal is equal to that of the third signal, but the present invention is not limited thereto, and the duration of the first signal may be set to be different from that of the third signal.

The duration of the fifth signal is controlled so that it is sequentially shortened, and when it reaches a certain value, the fifth signal is controlled so as to increase the duration. For example, from T510 to T517, using the duration of each fifth signal from T501 to T508, the control is performed so that the duration of the first signal, the third signal, and the fourth signal is sequentially increased, and the duration of the second signal is sequentially shortened. For example, T510 is controlled using T508, T511 using T507, T512 using T506, . . . and T517 using T501. Thereafter, T501 to T517 are repeated. It should be noted that in this example, a series of control (referred to as "one cycle"), in which the duration of the fifth signal is controlled to start at 1 second i.e. 1 Hz, and to increase by 0.5 Hz to a certain value e.g. 0.2 second i.e. 5 Hz, and when 5 Hz is reached, the duration of the fifth signal is controlled to conversely decrease by each 0.5 Hz to return to 1 Hz, is performed in about 7.5 seconds, and this series of control is repeated. The present invention is not limited this example, and any control may be used as long as one cycle is a series of control to vary by 0.03 Hz, for example, from 2 Hz to 5 Hz, and one cycle lasts for about 31 seconds.

In the control exemplified above, the duration of each signal constituting the fifth signal is changed with a change in the duration of the fifth signal. On the other hand, the control may be performed such that only a part of the duration of each waveform is changed. For example, controlling may be performed so that T101=T102=T103=T104= . . . =0.03 second, T201=T202=T203=T204= . . . 0.1 second, and T301=T302=T303=T304= . . . =0.03 second, i.e. these may be constant at all times, in which only the duration of the fourth signal may be controlled, so that, for example, T401=0.84 second, T402=0.51 second, T403=0.34 second, T404=0.24 second, . . . T409=0.04 second. On or after T510, on the contrary, the time corresponding to T4 is controlled so as to be successively increased. For example, the time corresponding to T4 is successively increased to 0.06 second, 0.09 second, 0.12 second, 0.17 second, 0.24 second, 0.34 second, 0.51 second, 0.84 second, and this process is repeated thereafter. In this example, the durations of the first signal, the second signal, and the third signal are constant, but the present invention is not limited thereto, and the control may be performed so that the duration of the first signal or the third signal may be constant, or so that one or both of the duration of the second signal and the duration of the fourth signal may be constant. Alternatively, the sum of the durations of a particular signal may be controlled to be constant. For example, such a control may be performed in which the sum of the durations of the first signal, the second signal, and the third signal is constant, however the lengths of the first signal and the second signal are changed.

In the control exemplified above, the duration of the fifth signal is changed every time the fifth signal is output. The present invention is not limited to this, and the control may be performed so that the duration of the fifth signal is changed as the fifth signal is output for a certain number of times; for example, after the fifth signal is output twice during the duration of T501, the fifth signal is output twice during the duration of T502, and subsequently the fifth signal is output twice during the duration of T503. Further, control may be performed so that the number of outputs of the fifth signal is controlled based on the duration of the fifth signal; for example, after the fifth signal is output once during the duration of T501, the fifth signal is output twice during the duration of T502, and subsequently the fifth signal is output three times at T503. In addition, a rate of change in the duration of each signal in the control to increase the duration of the fifth signal and a rate of change in the duration of each signal in the control to decrease the duration of the fifth signal may be changed. That is, when reducing the duration of the fifth signal, for example, to the duration may be decreased by 0.03 second, but, when increasing the duration, the duration may be increased by 0.05 second, and so on.

Figure 5A:
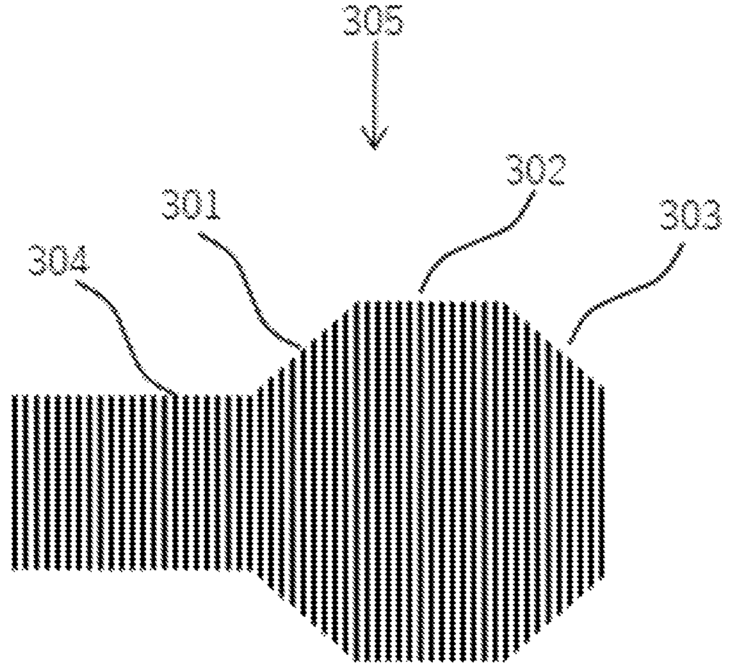
FIG. 5A is an explanatory view for explaining an electric signal for use in the current stimulation apparatus of the present invention.
Figure 5B:
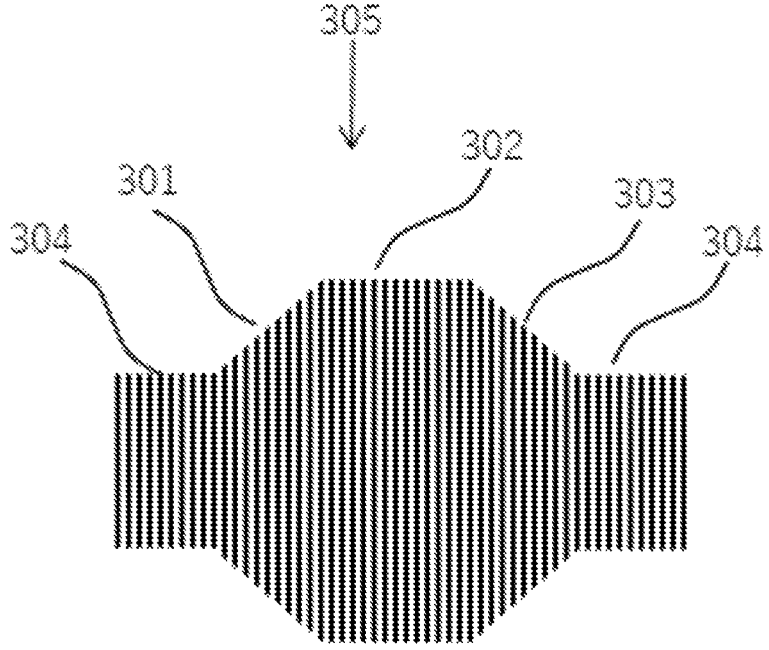
FIG. 5B is an explanatory view for explaining an electric signal for use in the current stimulation apparatus of the present invention.

FIG. 5 shows another example of the fifth signal in the present invention. In FIG. 4, the first signal, the second signal, the third signal, and the fourth signal are output in this order to form the fifth signal, but not limited thereto, for example, the fourth signal, the first signal, the second signal and the third signal may be output in the order to form the fifth signal as shown in FIG. 5A. Alternatively, as shown in FIG. 5B, the fourth signal, the first signal, the second signal, and the third signal may be output in this order, and then the fourth signal may be output again, to configure the fifth signal. Instead of the fourth signal output after the third signal in FIG. 5B, the sixth signal of which the amplitude is different from that of the fourth signal may be used to configure an electric signal. The signal configured using the first signal, the second signal, the third signal, the fourth signal, and the sixth signal may be used as the seventh signal, and the control as described above may be applied to the seventh signal.

As a state in which the amplitude is gradually changed just as the first signal or the third signal, the control is shown so that the amplitude varies for each basic pulse as described above; however, the present invention is not limited thereto, and the amplitude may be controlled to be varied in a stepwise manner in a uniform step or in a non-uniform step by control such that the amplitude is changed after a plurality of basic pulses are output. Alternatively, as shown in FIGS. 3 to 5, such control is also possible in which, the amplitude is changed nonlinearly, instead of changing the amplitude of the first signal and the third signal linearly at a constant rate.

Figure 6A:
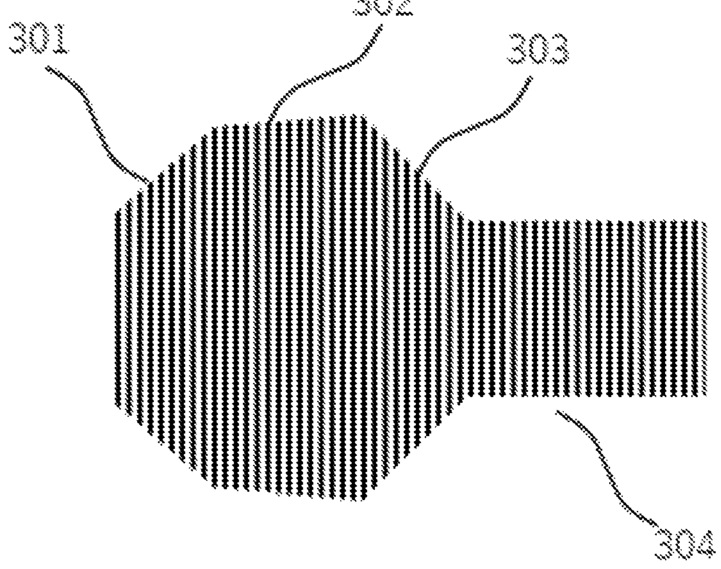
FIG. 6A is an explanatory view for explaining an electric signal for use in the current stimulation apparatus of the present invention.
Figure 6B:
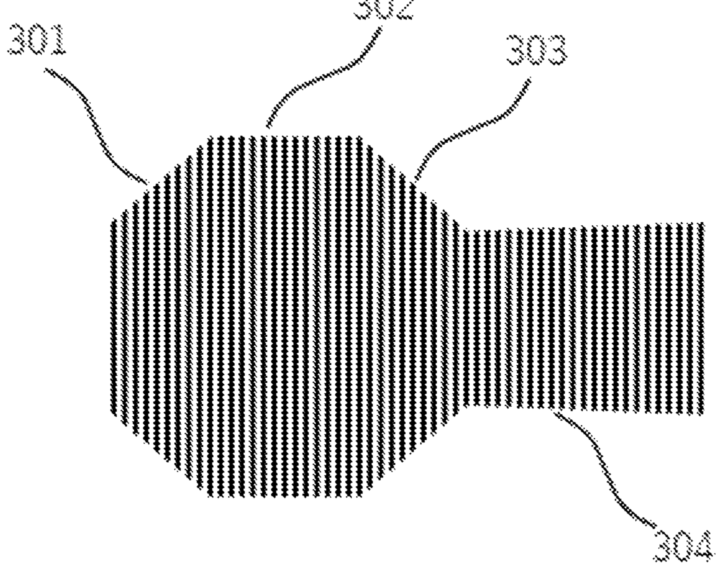
FIG. 6B is an explanatory view for explaining an electric signal for use in the current stimulation apparatus of the present invention.

As a state in which the amplitude is maintained as the second signal and the fourth signal, the above examples show the control such that the amplitude of the basic pulse does not change; but the present invention is not limited thereto, and such control is also possible in which the amplitude of the basic pulse is changed at least so that the amplitude does not fall below or exceed a certain value. Examples of this are shown in FIGS. 6A and 6B. FIG. 6A shows the control so that the amplitude of the second signal is not constant. FIG. 6B shows the case where the fourth signal is not constant. In the present invention, any control may be performed as long as the effect of high frequency electric signals and low frequency electric signals are appropriately obtained. The controls in FIG. 6A and FIG. 6B are alternatively used, and such control is also possible in which the amplitudes of both of the second signal and the fourth signal are not constant. Furthermore, these controls can be applied to the fifth signal as shown in FIG. 5. That is, the amplitude of each signals, from the first signal to the fourth signal, can be changed every time the fifth signal is output, and such control as shown in FIG. 6A and FIG. 6B can also be applied.

In each of the above examples, only the amplitude of the basic pulse is controlled to realize the control of each signals; however, not limited thereto, at least the pulse width, frequency, or maximum amplitude of the basic pulse may be varied. For example, instead of lengthening the duration of the second signal, the pulse width may be controlled to set longer than 100 μsec. For example, instead of the duration of the second signal being longer as 0.005 second, 0.01 second, 0.015 second, 0.02 second, 0.025 second, 0.03 second, 0.035 second, 0.04 second, 0.045 second, the pulse width of the second signal can be controlled to be, for example, 100 μsec, 150 μsec, 200 μsec, 250 μsec, 300 μsec, 350 μsec, 400 μsec, 450 μsec, by controlling the duration of the second signal to be constant. The use of this pulse width control does not exclude the control of the duration of each signal, e.g. the duration of the second signal, and it is possible to use both of the pulse width control and the signal duration control. Thus, for example, such control may be possible in which, the duration of the second signal is increased as 0.005 second, 0.01 second, 0.015 second, 0.02 second, 0.025 second, 0.03 second, 0.035 second, 0.04 second, 0.045 second, and the pulse width of the basic pulse may be controlled to be, for example, 100 μsec, 150 μsec, 200 μsec, 250 μsec, 300 μsec, 350 μsec, 400 μsec, 450 μsec. To be more specific, the control may be performed to change both the duration and the pulse width of the second signal, such as 100 μsec for the pulse width when the duration of the second signal is 0.005 second, 150 μsec when the duration is 0.01 second, 200 μsec when the duration is 0.015 second, 250 μsec when the duration is 0.02 second.

Although the amplitude of each signal in the present invention may be to be individually set, the first amplitude, the third amplitude, and the fourth amplitude may be changed in conjunction with the second amplitude, for example. Therapeutic methods using electric signals as described above are extremely effective and can improve therapeutic efficiency.

Second Embodiment

Figure 7A:
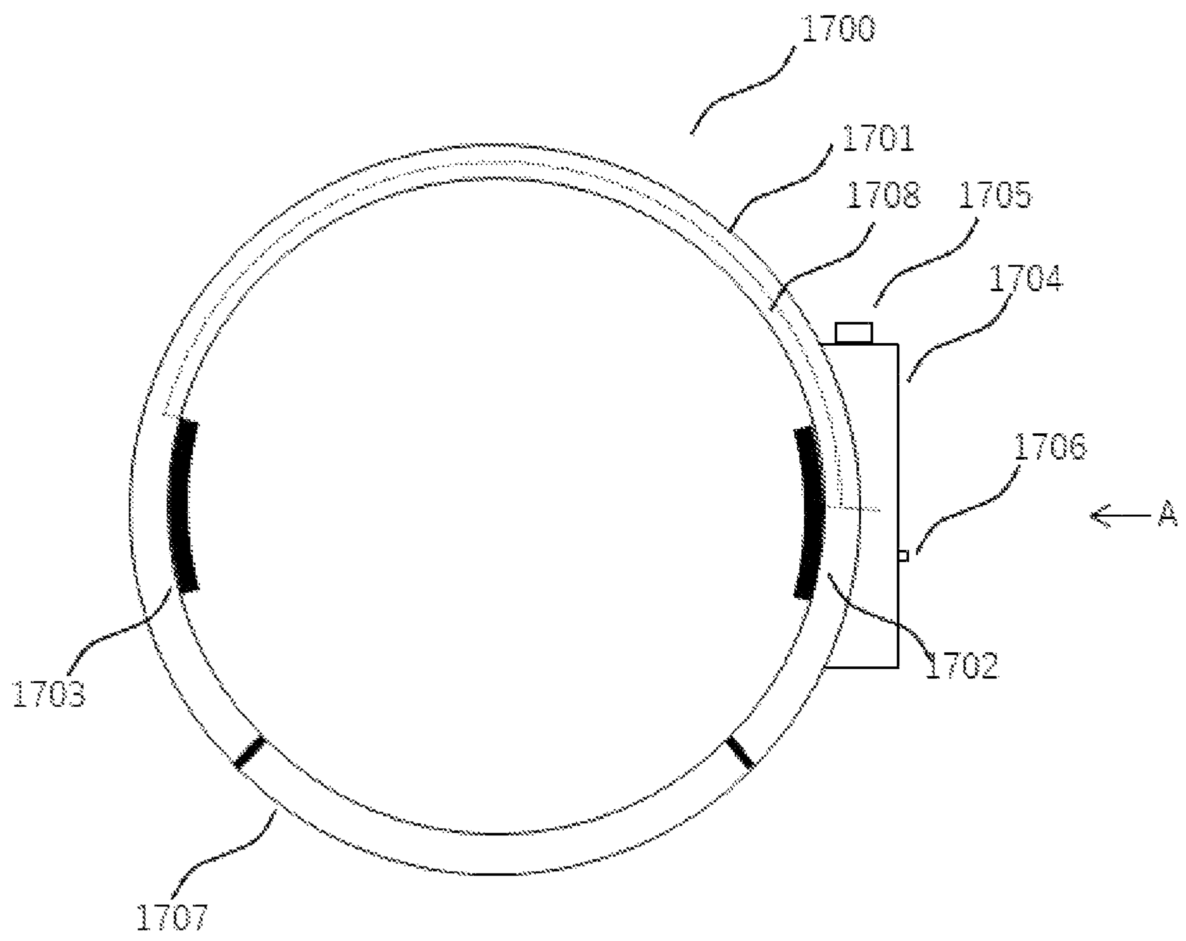
FIG. 7A is an explanatory view for explaining an electric signal for use in the current stimulation apparatus of the present invention.
Figure 7B:
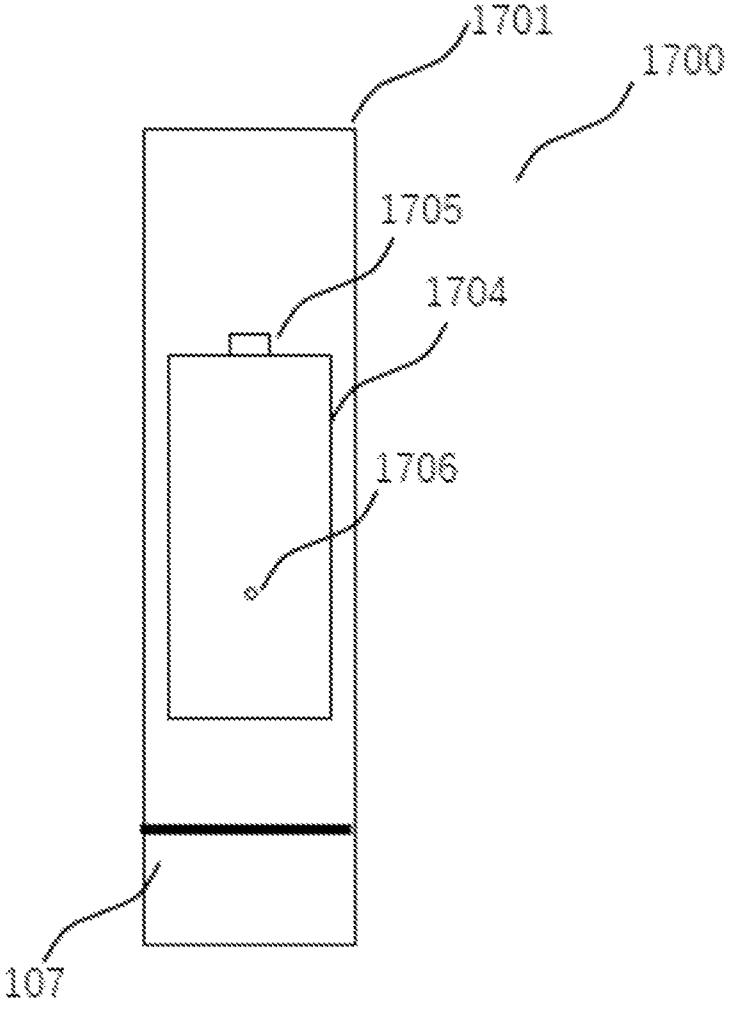
FIG. 7B is an explanatory view for explaining an electric signal for use in the current stimulation apparatus of the present invention.

Other examples of current stimulation apparatuses of the present invention are described. FIG. 7A shows an external side view of a main body A1700 of the current stimulation apparatus according to the present disclosure. The main body A1700 comprises a belt part A1701, an elastic part A1707, and the controller A1704. An electrode A1702 as the first electrode and an electrode B1703 as the second electrode are provided on the belt part A1701, the first electrode and the second electrode contact the human body and are connected to the controller A1704 by a harness A1708 provided inside the belt part A1701. Since the harness A1708 is not visible from the outside, only the position of the harness is indicated by dotted line. FIG. 7B is a front view of the main body A1700 as viewed from the direction of arrow A in FIG. 7A.

The elastic part A1707 is made of, for example, silicone rubber, to be capable of expansion/contraction easily and, to expand and contract the elastic part A1707, makes it possible to wear the main body section on the limb, e.g. wrist. The electrode A1702 and the electrode B1703 when mounted, can be brought into contact with the skin of a wrist to impart an electric stimulus as described later. The part to which the main body A1700 is mounted is not limited to a wrist, but may be the ankle, and it is desirable to mount the main body A1700 at or near a distal portion. In particular, it is desirable to attach to a wrist or an ankle, by considering such as ease of wearing, difficulty in detachment, and handling in use. In this embodiment, the main body A1700 is described as being worn on a wrist. The elastic part A1707 may be made of a natural rubber or a urethane rubber, not limited to silicone rubber.

The main body A1700 is positioned so that the controller A1704 is on the back of the wrist and the electrode A1702 comes into contact on the back of the wrist and the electrode B1703 on the palm side of the hand of the wrist. Conversely, the controller A1704 may be attached on the palm side of the hand, and the electrode A1702 may come into contact on the palm side of the wrist and the electrode B1703 on the back of the wrist.

The main body A1700 is formed in an annular shape by the belt part A1701 and the elastic part A1707, but does not have to be a circle, and may have, for example, an oval shape or a polygonal shape such as a rectangular shape or may any other shape as long as the electrode A1702 and the electrode B1703 are appropriately contacted to the wrist.

The belt part may be formed into a belt shape instead of an endless annular shape, and fixing means such as a hook-and-loop fastener, a button, or a hook may be attached to both ends, and may be formed into an annular shape by being fixed by a hook-and-loop fastener, for example, by being wrapped around a wrist or the like. Alternatively, a belt part in a belt shape which is partially released may be formed by using, for example, an elastic plate spring or the like having a release end, which is not endless even if it is worn, so that the attachment and detachment are facilitated by the elasticity of the plate spring and the contact between the electrode and the skin can be easily and reliably carried out.

The electrode A1702 or the electrode B1703 may be composed of a solid gel, for example, which is highly conductive or electrically low resistive. However, the present invention is not limited to this, and a conductive member may be used in which electrodes are appropriately contacted to a portion to which the main body A1700 is attached and electric signals can be applied to the skin. The conductive member may be, for example, a metal such as a stainless plate molded in the form of an electrode, or may be a conductive cloth using silver yarn or the like, or may be a conductive paint. Alternatively, conductive rubber may be used, for example, conductive rubber having conductivity by mixing conductive material typified by carbon powder using silicon rubber or urethane rubber as a base material.

A switch A1705 and an LED-A1706 are provided on the controller A1704, by which the electric signal applied to the electrode A1702 or the electrode B1703 can be controlled and checked. By pressing the switch A1705, the LED-A1706 is turned on, and an electric stimulus, which will be described later, is supplied to a distal portion of the limb, i.e., a wrist in this embodiment, through the electrode A1702 and the electrode B1703.

In this embodiment, the controller A1704 has a controller 17 as shown in FIG. 2, but a battery 1773 is provided instead of the power supply section 206 in FIG. 2 in the controller 17 for use in this embodiment. The battery 1773 may be, for example, a button-type battery or a repeatedly rechargeable battery, such as lithium-ion battery. Alternatively, the battery 1773 (not shown) may be replaced with a configuration to be used by being connected to a DC power supply using a household outlet.

The main body A1700 outputs, for example, the electric signals described in the first embodiment described above. The electric signals shown in FIG. 3A and FIG. 3B are output, for example, of which the frequency of the basic pulse is 5 Hz, of which the pulse width is 50 msec, of which the second amplitude is 300 μA, of which the fourth amplitude is 100 mA, and of which T1 to T4 is respectively 1 second.

As the electric signal in the present embodiment, an output by which the human body cannot sense electric stimulation (hereinafter, referred to as "unfelt output") is used. Generally, when the current value exceeds 20 mA, pain due to the current is likely to occur. As can be seen from FIG. 8-20, in P. 242, second edition of EBM Physical Therapy (Ishiyaku Shuppan Co., Ltd.), muscular contraction requires an output of 20 mA or more. Conversely, if the output is 20 mA or less, electric signals application is felt, but muscular contraction is unlikely to occur. In addition, a value of 300 μA, or 100 μA as in this example does not normally cause muscular contraction; and in addition, unless there are special conditions, people cannot usually feel the electric signals supply, and of course, do not feel pain caused by the electric signals.

In the present invention, by applying the above-mentioned electric signal to the distal portion of the limb or in the vicinity of that portion using only one set of electrodes, the effect can be obtained on the whole body, specifically, the effect of adjusting the autonomic nerve can be obtained. As described above, the set of the electrodes A1702 and the electrodes B1703 are arranged on the palm side of the wrist and the back side of the hand. Normally, the effect is limited to the muscles through which the current flows, but in the present invention, there are no nerves or muscles along the current flowing by the electrodes in the region where the electrodes are attached, that is, in the wrist, and the effect that the autonomic nerve is adjusted is not an effect due to stimulation of specific nerves or muscles by the applied electric signal. According to the present invention, the specific effect of adjusting the balance of the autonomic nerve can be obtained by applying the electric stimulation to the distal portion of the limb or the vicinity of that portion. Also, the effect persists for a long time even if the supply of the electric signal is stopped, and this persistence is also an effect peculiar to the present invention.

As described above, the autonomic nervous system can be balanced, and therefore, for example, if the sympathetic nerve is excessively dominant, the sympathetic nerve function can be suppressed or the parasympathetic nerve can be activated, and conversely, if the parasympathetic nerve is excessively dominant, the parasympathetic nerve function can be suppressed and the sympathetic nerve can be activated, so that the sympathetic nerve and parasympathetic nerve can be balanced. If the sympathetic nerve is dominant due to internal disease or the like, sleep is insufficient in some cases, and the physical condition may be further disrupted due to sleep deficiency or sleep deprivation stress, but it is desirable to use a device to which the present invention is applied, thereby to balance the autonomic nervous system, and obtain favorable quality sleep, and therefore psychological stress is also relieved. Conversely, when the parasympathetic nerve is excessively dominant, the parasympathetic nerve can be suppressed, and the sympathetic nerve can be activated, sleepiness can be suppressed to improve the efficiency of driving, working, studying, and the like, and the stress about sleepiness can also be solved.

The present invention is not limited to the above embodiments. Hereinafter, as another embodiment, a modification of each of the above embodiments will be described. Further, the following modifications may be used in combination with the main body A1700 describes above, or at least two of the following modifications and the above embodiments may be combined.

Figure 8:
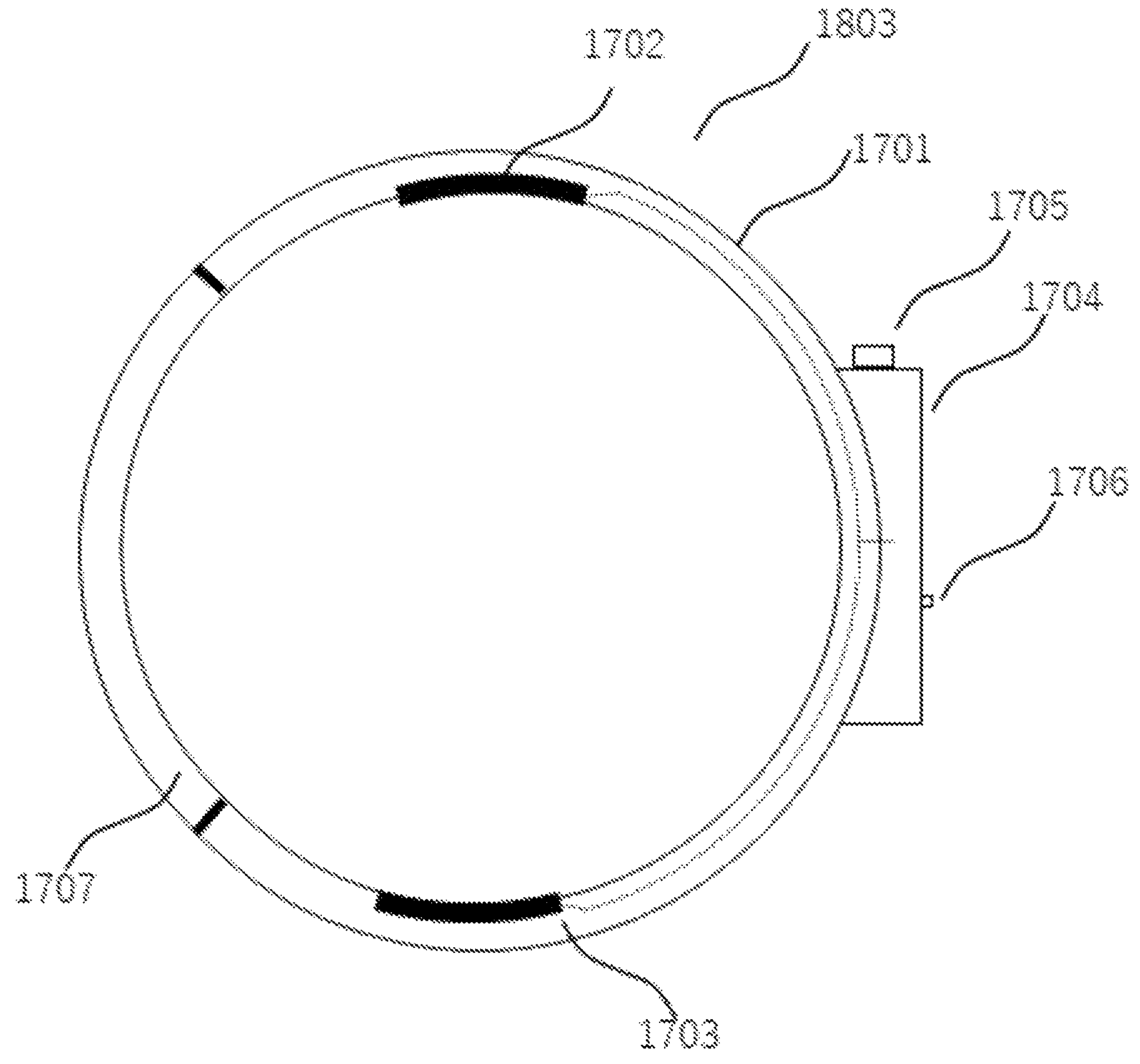
FIG. 8 is an explanatory view for explaining an electric signal for use in the current stimulation apparatus of the present invention.

FIG. 8 shows one modification of a main body C1803. Regarding the main body A1700 described above, the controller A1704 is attached on the back side or the palm side of the wrist so that the electrode A1702 and the electrode B1703 are on the back side or the palm side of the hand. But the electrodes may be arranged on the right side and the left side of the wrist toward the back side or the palm side of the wrist as shown in the main body C1803 of FIG. 8, i.e., may be arranged to sandwich the wrist from the left and right, or may be arranged side by side on the wrist. For example, the electrode A1702 and the electrode B1703 may be arranged side by side so as to be adjacent along the circumferential direction of the wrist at the belt part A1701; however, the electrodes may be arranged side by side so as to be perpendicular to the circumferential direction, or may be arranged obliquely against the circumferential direction. Thus, with respect to the placement of the electrodes, because the present invention is not designed for direct muscle contraction by electric signals or stimulation of a particular acupressure point, the present invention can place the electrodes regardless of the direction of the muscle, the location of the acupressure point, the presence or absence of the muscle or the acupressure point, or regardless of the muscle along the electrical flow path. FIG. 8 shows a main body C1803 in which the electrode position of the main body A1700 is changed as an example, but in a device provided with the present invention which provides an electric current to the distal portion of the limb or the periphery of the portion, and in each later-described examples, the electrode may be arranged as in this figure.

Another modification is shown. The output of the electric signal used in the above is 300 μA as the second amplitude, but this is not limiting, and for example 200 μA, 100 μA, or 500 μA etc. may be used. Though being 100 μA in the above, the fourth amplitude may be, for example, 50 μA. Alternatively, output values may be adjusted so as to achieve desired effects, e.g., the output may be adjusted by providing the controller A1704 with a volume function. There are individual differences in the above-mentioned effects, so that it is desirable if the output is adjustable.

Another modification is shown. With respect to the output of the electric signal used in the above, the output of the second signal is only one value of 300 μA, for example, but this is not limiting. For example, with respect to the second signal, the output value may be changed from 300 μA, for each of the fifth signal. For example, immediately after switch A1705 is pressed, i.e. the initial output of the second signal is 300 μA, but the output of the second signal may be 320 μA, and thereafter the output value may be changed gradually for each of the fifth signal. Alternatively, the output value may be increased or decreased. Similarly, the fourth amplitude may be changed for each fifth signal.

Another modification is shown. With respect to the output of the electric signal used in the above, the output used for the second signal, for example, is 300 μA as described above, and an output in which the human body cannot sense the electric stimulation is used; but the present invention is not limited to this. Output in such a range that electric stimulation can be sensed in the wrist and muscle contraction does not occur and pain is not sensed due to the electric stimulation (hereinafter referred to as "felt output"), for example, an output about 500 μA or 800 μA may be used. Here, 500 μA is described as a felt output. Thus, at 500 μA, if there is no scratch or the like on the wrist, or current concentration as described later, most people do not seem to feel pain.

Another modification is shown. The output of the electric signal used in the above is a constant output, but the present invention is not limited to this. Immediately after the start of the output, the output is a felt output, e.g., 500 μA. It is possible to configure such that, after a predetermined time from the start of output, for example, 30 seconds has passed from the start of the output, the output of the electric signal is changed to an unfelt output, for example, 100 μA. The output may be, for example, directly changed from a felt output to an unfelt output, i.e., 500 μA to 100 μA, or gradually changed from 500 μA to 400 μA, 300 μA, . . . , and finally to 100 μA. The felt output is a very weak power so that no pain is felt as described above, and therefore can be used as the second signal, and even if the felt output using 500 μA is used in combination with the unfelt output, the same effect as that of the unfelt output can be obtained, and the effect of the unfelt output is not inhibited. For example, the use of a felt output does not reduce the effect of an unfelt output, and there is no problem or no harm caused by the use of a felt output. Therefore, the temporary use of the felt output leads to make the effect of the unfelt output more effective described as follows.

In the case of using an unfelt output, there is a problem that the user cannot recognize the absence of output for such reasons as because the user cannot sense the absence of proper output when the user fails to press the switch A1705, or when the charge remaining of the battery 1773 is little. However, by using the felt output after the start of output as described above, the user can easily know that the electric signal is output. On the contrary, the user can easily know the absence of the output in the case that the user cannot sense a felt electric stimulation immediately after the start of output, and such a problem can be easily avoided. For example, it is easy to notice that the switch has been operated incorrectly or that the battery has run out, and it is easy to operate the switch correctly or it is easy to change or charge the battery 1773. In addition, in the case that only an unfelt output is used, the user cannot sense the electric stimulation so that the user may wonder whether the electric signal is really output, i.e., whether the device is working properly. However, due to a temporally sensible electric stimulation, the user can easily know the normal operation of the apparatus, and can realize the output.

The temporary felt output as described above is not only immediately after the output starts, but also before the output ends. For example, the felt output instead of unfelt output for 30 seconds before the output ends can make the user know that the output will be terminated soon. When an unfelt output is used, there is a problem that the user cannot know when the output is finished, but since the felt output is used at the end of the output, the user can easily know the end of the output. It is possible to change from the unfelt output to the felt output directly, for example, when the unfelt output is 100 μA, the output may be directly changed from 100 μA to 500 μA, or the output may be gradually changed from 100 μA to 200 μA, 300 μA, and finally to 500 μA The temporary felt output as described above can be used not only at the start of the output or at the end of the output, but also both at the start and at the end of the output. Alternatively, periodically using a temporary felt output can inform the user that the device is operating normally and inform the passage of time. For example, a felt output may be used as the second signal or as the second and the fourth signals every 5 minutes of the continuous output. In addition, it is more desirable to change the duration of the felt output (standing for the passage of time) used when the output continues from the duration of the felt output used at the end of the output so that the user can judge whether the felt output means ending of the output or the passage of time if the user feels the felt output.

As described above, the use of the felt output for a short time at the beginning of the output, at the end of the output, or periodically, that is, the use of the temporary felt output, is more desirable in the following respects. Although a felt output does not cause a person to feel pain, it does not always mean that feeling a felt output for a long time gives people no stress. Therefore, even if a felt output does not cause pain, it is desirable that a felt output is limited to a short-term use or a temporary use, and it is more desirable that such a felt output is used temporarily instead of an unfelt output in order not to cause stress to the user. As described above, when the unfelt output is used, a temporary felt output can be used as a notification method or a notification means, in order to inform the user of information indicating the beginning of the output or the end of the output of an electric signal, or the passage of time, etc.

Figure 9A:
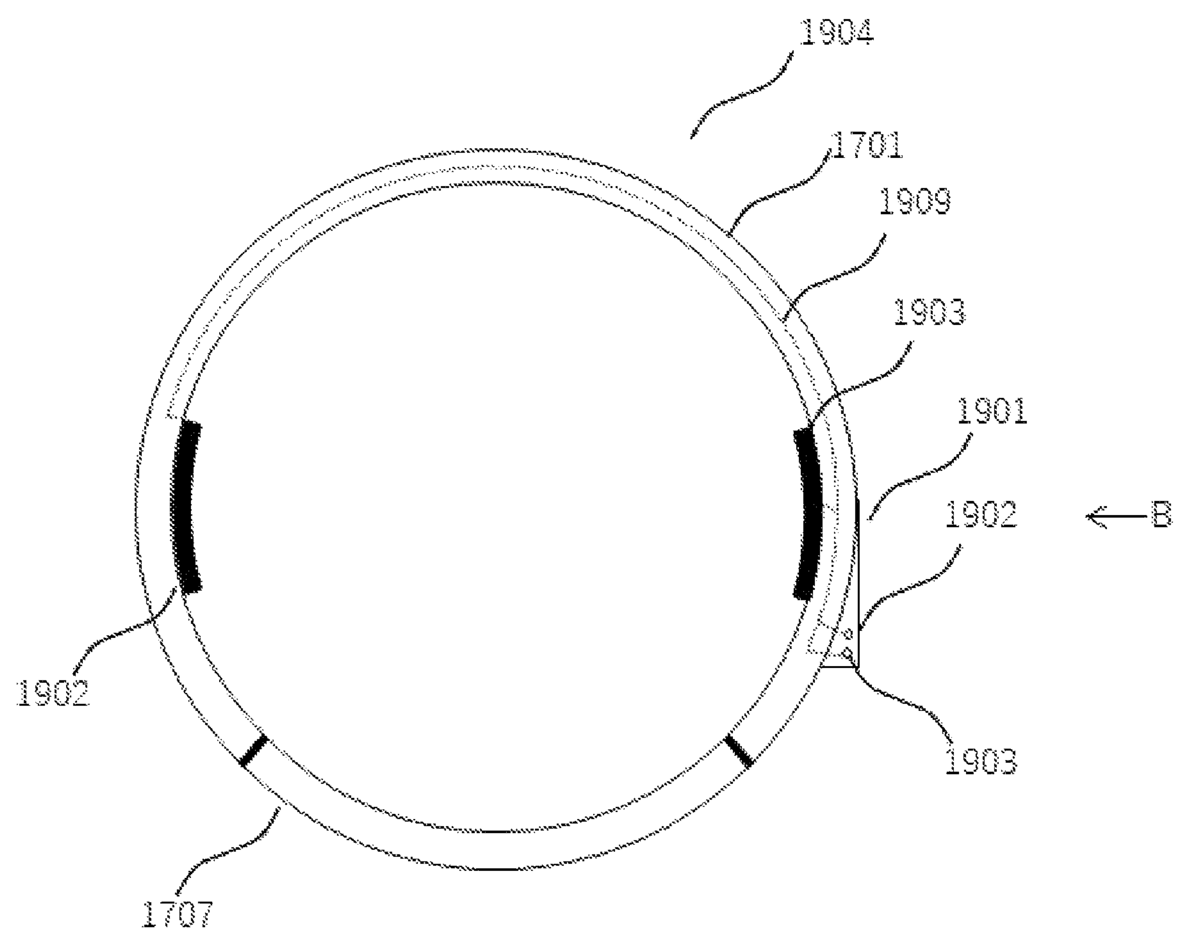
FIG. 9A is an explanatory view for explaining an electric signal for use in the current stimulation apparatus of the present invention.
Figure 9B:
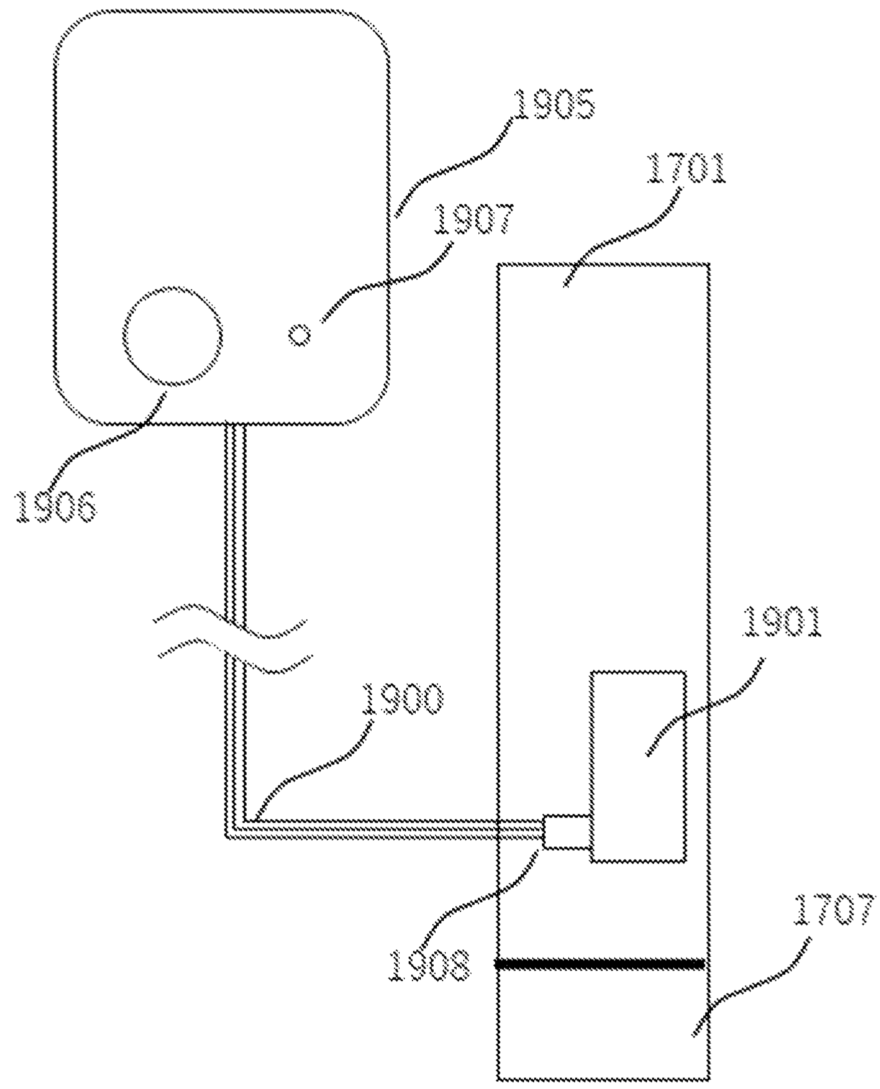
FIG. 9B is an explanatory view for explaining an electric signal for use in the current stimulation apparatus of the present invention.

FIGS. 9A and 9B illustrate a main body D1904 that is another modification. As described above, in the main body A1700, various types of circuitry portions built in the controller A1704 are provided on the belt part A1701. But this is not limiting and such circuitry portions may be provided other than on the belt part A1701. As shown in FIG. 9B, for example, a controller D1905 may be provided as a separated body which is separated from the main body D1904. FIG. 9B shows an appearance seen from the direction of the arrow B in FIG. 9A. In FIG. 9A, the controller D1905 is omitted, but is shown in FIG. 9B. In this instance, the controller D1905 as the separated body may be configured for use around the neck, with a neck strap, for example, or may be configured for use in a pocket. In this case, the controller D1905 is connected to a terminal part A1902 and a terminal part B1903 of a mounting part 1901 provided on the belt part A1701 by a cable M1900 and a connector K1908, so that the electric signal may be provided to the wrist with the electrode A1702 connected to the terminal part A1902 and the electrode B1703 connected to the terminal part B1903. Each terminal part is connected to each electrode by a harness B1909 in the belt part A1701. A switch B1906 and an LED-B1907 are provided in the controller D1905, and are used similarly to the switch A1705 and the LED-A1706.

Figure 10A:
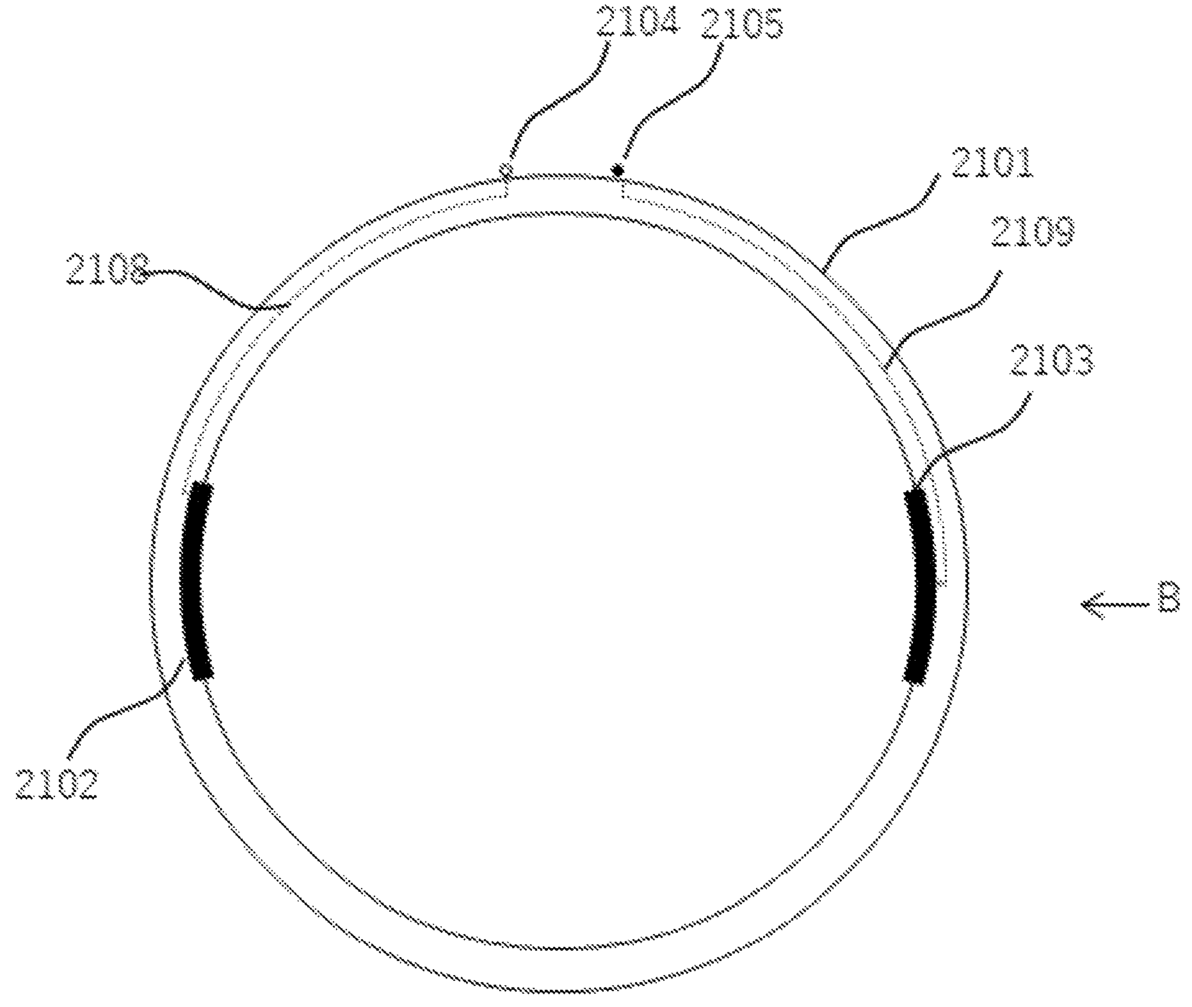
FIG. 10A is an explanatory view for explaining an electric signal for use in the current stimulation apparatus of the present invention.
Figure 10B:
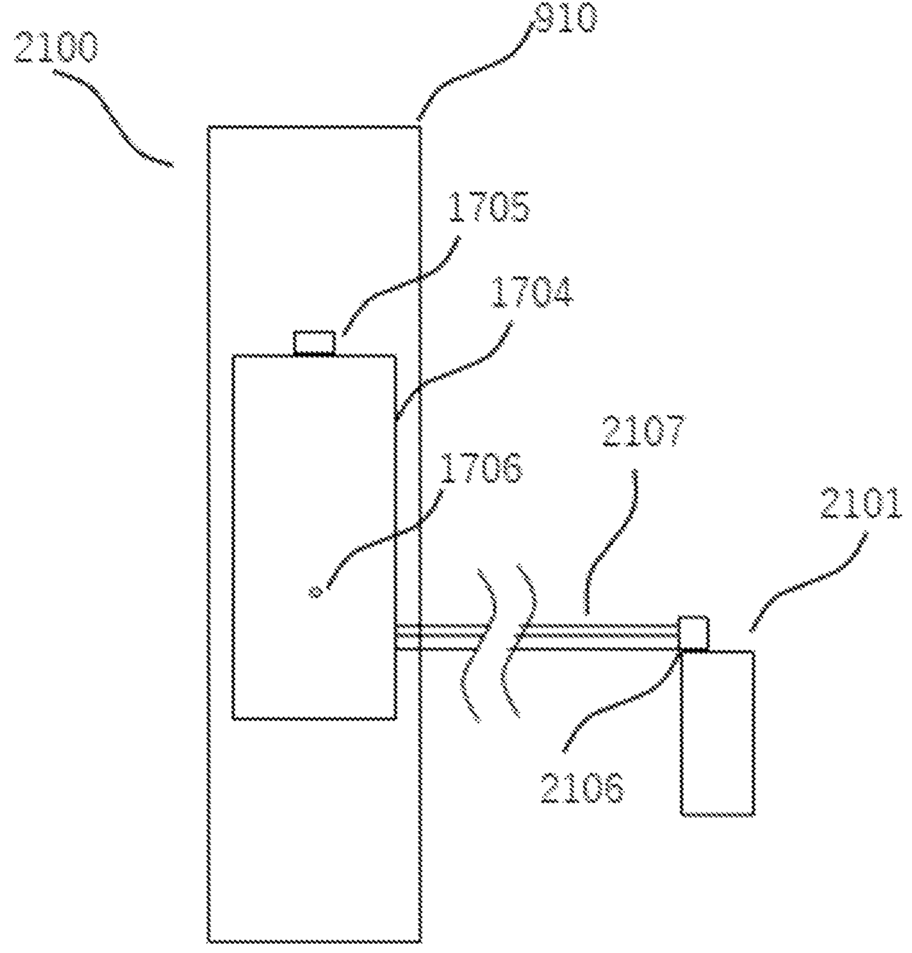
FIG. 10B is an explanatory view for explaining an electric signal for use in the current stimulation apparatus of the present invention.
Figure 10C:
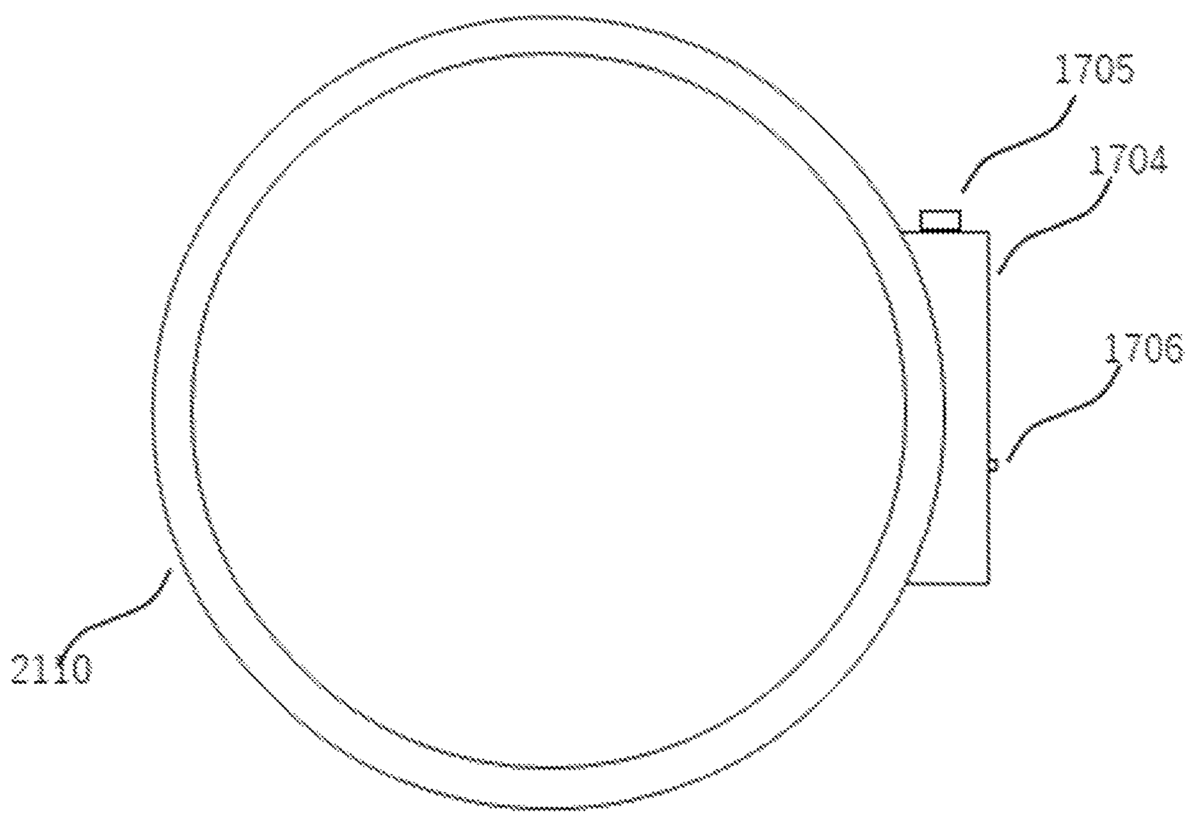
FIG. 10C is an explanatory view for explaining an electric signal for use in the current stimulation apparatus of the present invention.

FIG. 10A shows another modification. In the above examples, wearing on the wrist is assumed, but the present invention is not limited to this, and for example, a ring shape may be used, and as an example, a ring A2101 is shown. An electrode C2102 and an electrode D2103, corresponding to the electrode A1702 and the electrode B1703, are provided on the ring A2101. The electrode C2102 is connected to a terminal part C2104 by a harness C2108, the electrode D2103 is connected to a terminal part D2105 by a harness D2109, and the terminal part C2104 and the terminal part D2105 are connected to a cable H2107 by a connector H2106 so that the ring A2101 is connected to a main body H2100 configured by a bracelet 2110 on which a controller is provided. FIG. 10B shows a case where the controller A1704 is used. As shown in FIG. 10C, the controller A1704 is provided on the bracelet 2110, the main body H2100 is worn on the wrist, and the ring A2101 is worn like a finger ring for use.

The ring A2101 only needs to be an insulator such as resins, and may be, for example, rubber or silicone. FIG. 10A to FIG. 10C are conceptual diagrams to explain the configuration of each part. Thus, although the ring in FIG. 10A and the main body H2100 in FIG. 10C are drawn in about the same size, it does not mean that both of them are the same size.

Figure 11A:
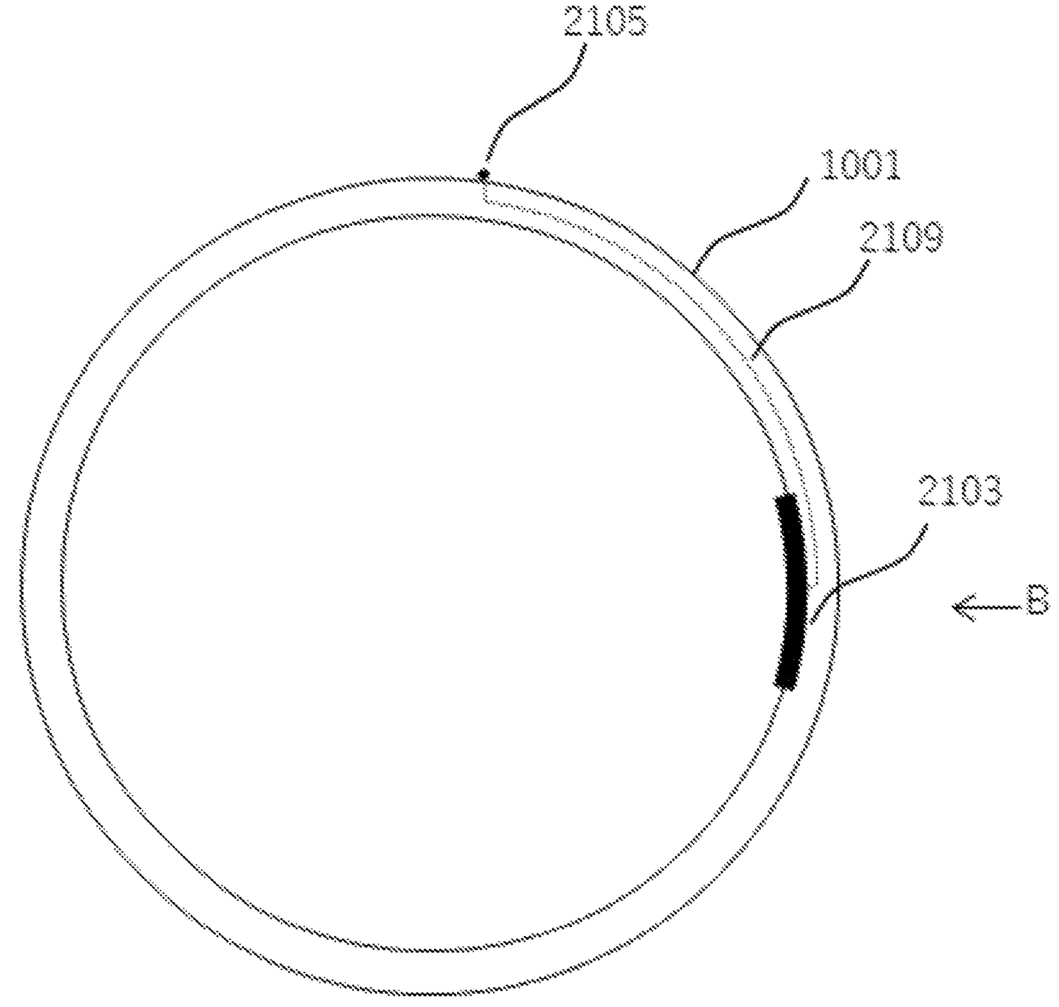
FIG. 11A is an explanatory view for explaining an electric signal for use in the current stimulation apparatus of the present invention.
Figure 11B:
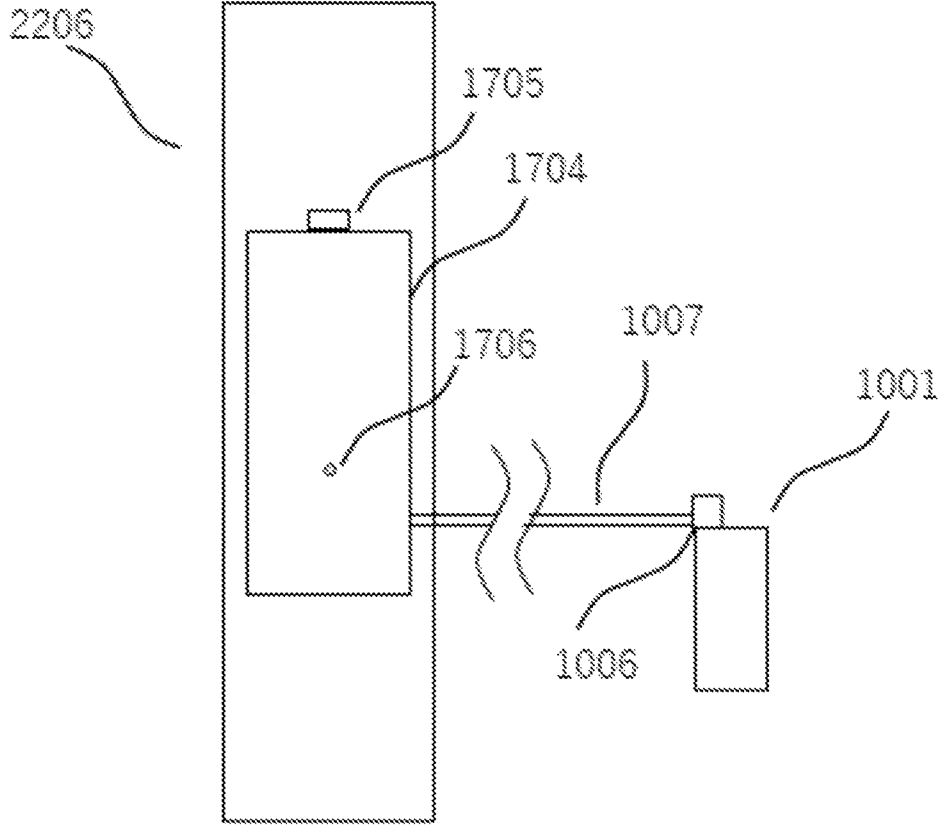
FIG. 11B is an explanatory view for explaining an electric signal for use in the current stimulation apparatus of the present invention.
Figure 11C:
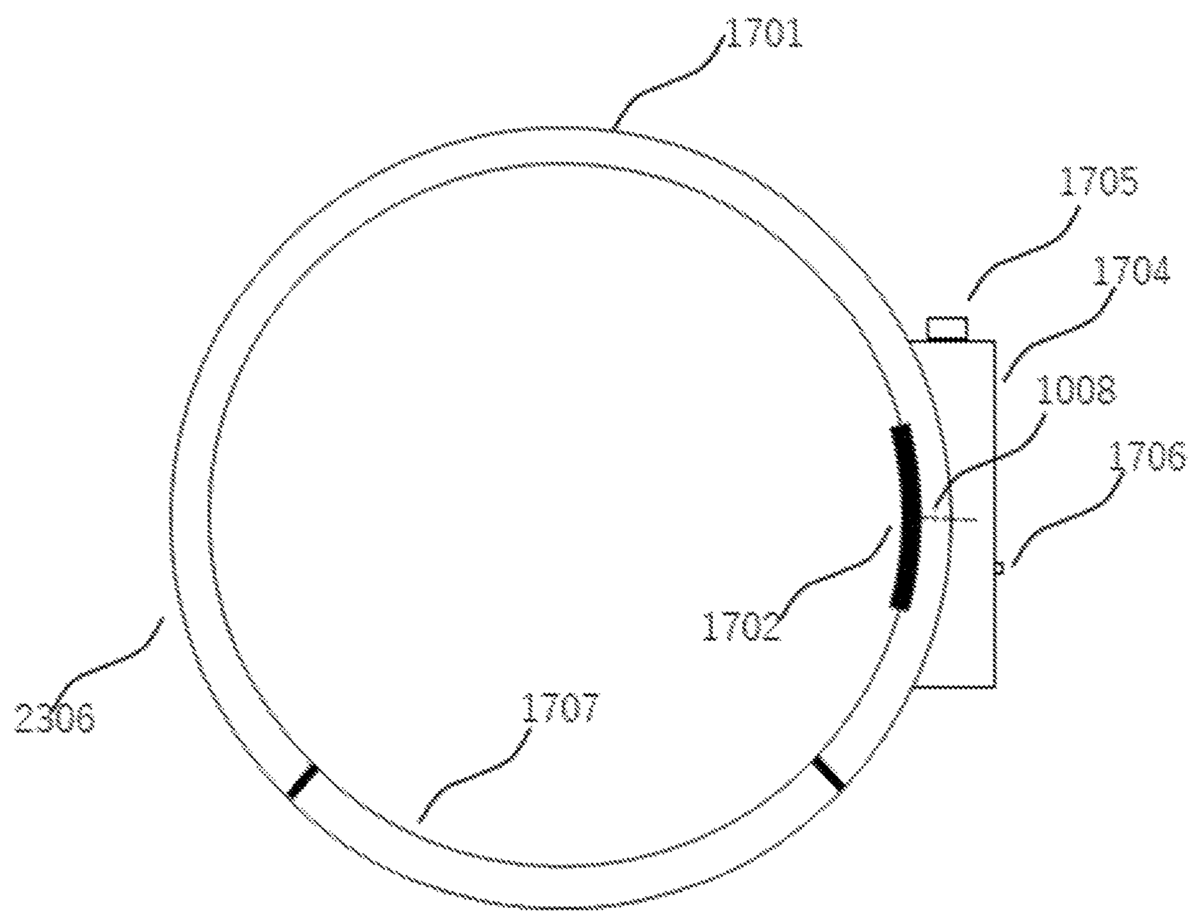
FIG. 11C is an explanatory view for explaining an electric signal for use in the current stimulation apparatus of the present invention.
Figure 11D:
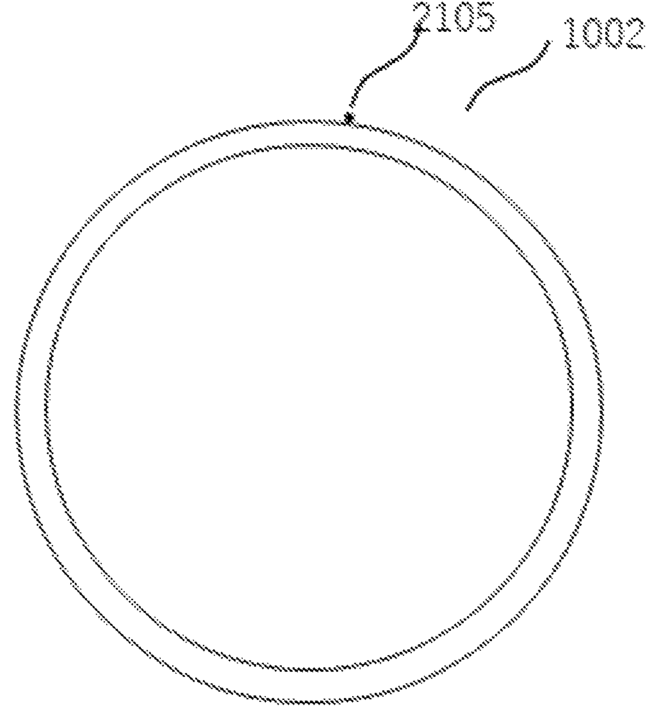
FIG. 11D is an explanatory view for explaining an electric signal for use in the current stimulation apparatus of the present invention.

FIG. 11A shows a modification of FIG. 10A to FIG. 10C. Although FIG. 10A shows a configuration in which two electrodes are arranged on the ring A2101, the present invention may use any configuration as long as the current is applied to the distal portion of the limbs or to the vicinity thereof, and the present invention is not limited thereto. For example, as shown in FIG. 11A, only one of the two electrodes to supply the electric signal may be provided on a ring J1001 in the shape of a ring and another electrode may be to be worn on a wrist. FIG. 11A shows the ring J1001 in the shape of a ring similar to FIG. 10A. However, the electrode C2102, the harness and others in FIG. 10A are not arranged on the ring J1001 but are arranged as an electrode A1702, a harness E1008 on a main body J2206 as shown in FIG. 11C. The main body J2206 comprises the belt part A1701 and the elastic part A1707, and has a configuration that is the same as that in FIGS. 7A and 7B. An electrode D2103 is connected to the terminal part D2105 via the harness D2109, the terminal part D2105 is connected to a cable J1007 by a connector J1006 and is connected to controllers. The main body J2206 is worn on the wrist and the ring J1001 is worn as a ring in use. As the configuration of the ring J1001, one example of using an insulating material as the ring A2101 is illustrated, but the present invention is not limited thereto so that the ring may be made of, for example, a conductor such as platinum or silver or a highly conductive material, as a ring K1002 in FIG. 11D. In this case, the harness D2109 and others are unnecessary and a simpler structure is possible. In FIG. 11B, the ring K1002 can be used instead of the ring J1001. The ring K1002 can be connected to the main body J2206 by a harness E1008 and the terminal part D2105.

Figure 12A:
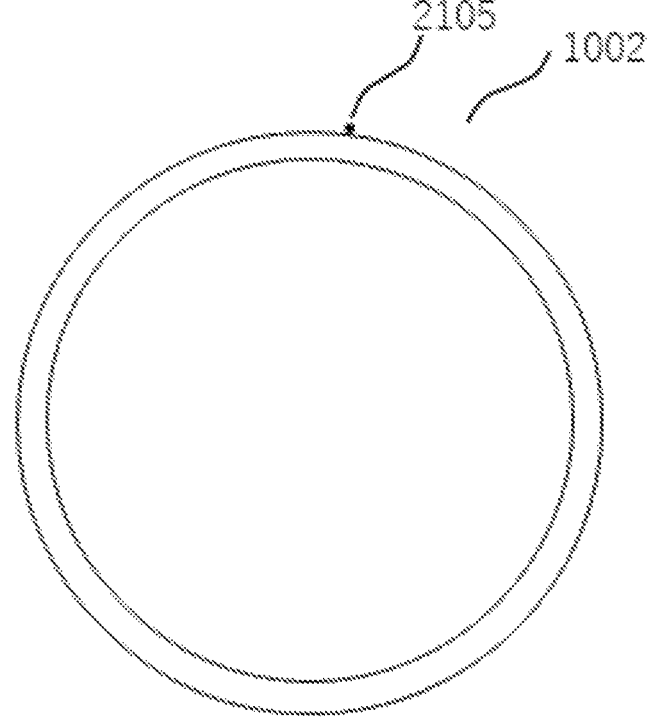
FIG. 12A is an explanatory view for explaining an electric signal for use in the current stimulation apparatus of the present invention.
Figure 12B:
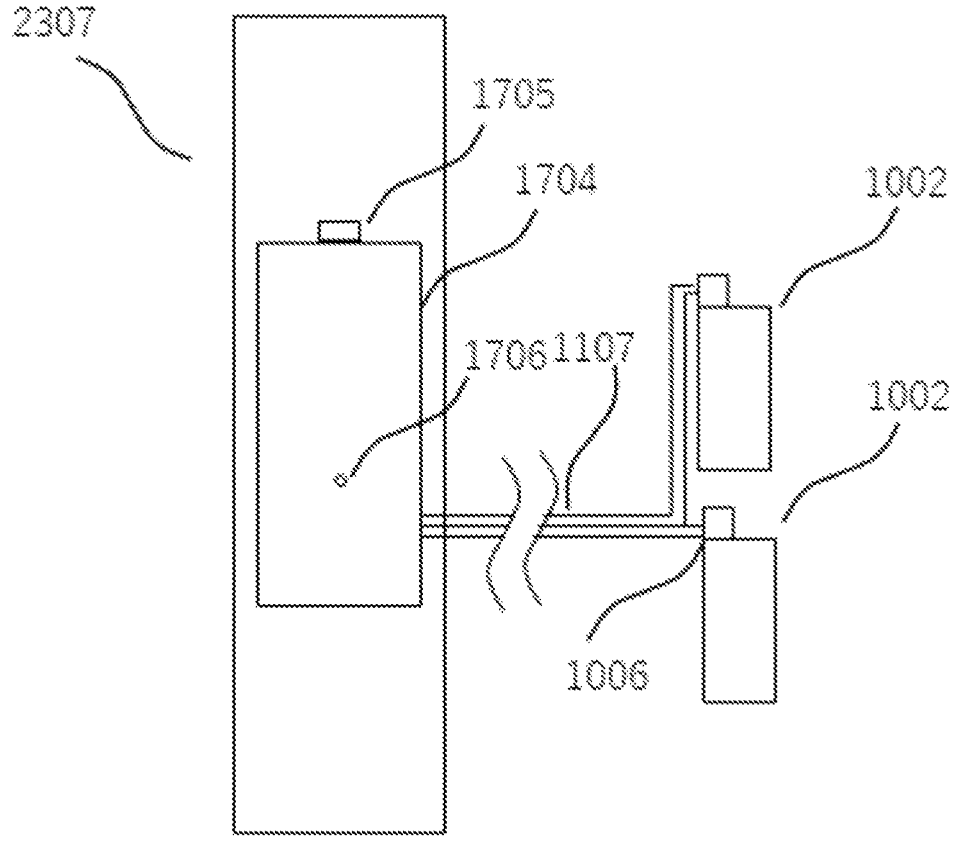
FIG. 12B is an explanatory view for explaining an electric signal for use in the current stimulation apparatus of the present invention.
Figure 12C:
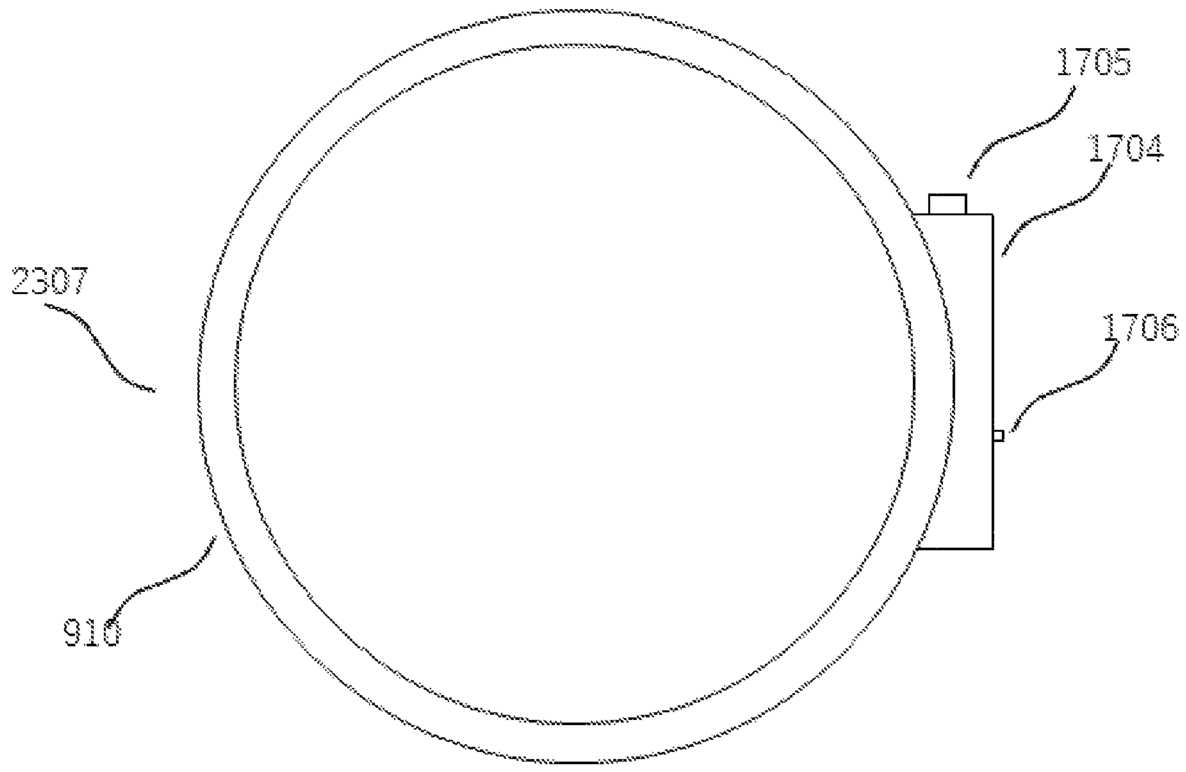
FIG. 12C is an explanatory view for explaining an electric signal for use in the current stimulation apparatus of the present invention.

FIG. 12A to 12C show other modifications. Each of FIG. 10A to FIG. 10C and FIG. 11A to FIG. 11D, shows an example in which only one ring such as the ring A2101, the ring J1001, or the ring K1002, is used, but the present invention is not limited to this example, and a plurality of rings, for example the rings K1002, may be used. The FIG. 12B shows a configuration in which two of the rings K1002 are used. In this figure, a main body K2307 which can use a plurality of the ring K1002 is used instead of the main body J2206, two of the rings K1002, acting as an electrode, are connected to the main body K2307 by a cable K1107.

Figure 13A:
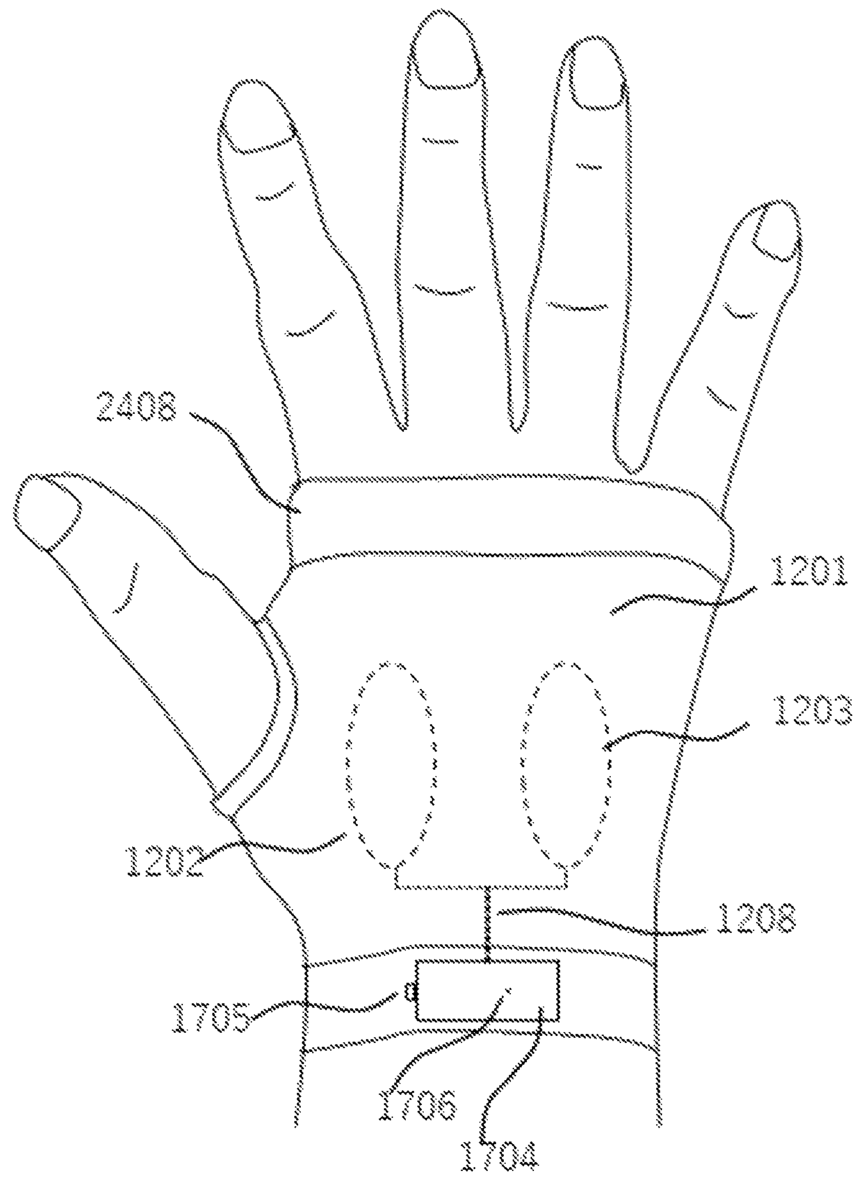
FIG. 13A is an explanatory view for explaining an electric signal for use in the current stimulation apparatus of the present invention.

FIG. 13A illustrates other modifications. The above description assumes wearing on a wrist or a finger, but the present invention is not limited to this, and for example, a supporter shape may be adopted. A main body L2408 is shown as such an example. The main body L2408 has a supporter 1201, an electrode E1202 and an electrode F1203 corresponding to the electrode A1702 and the electrode B1703 are arranged, and the electrode E1202 and the electrode F1203 are connected to the controller via a harness F1208. In FIG. 13A, the electrode E1202 and the electrode F1203 are arranged so as to contact the back of the hand, and since the harness F1208 is also provided inside the supporter 1201, the electrode E1202 and the electrode F1203 cannot be viewed directly from the outside, so their positions are shown by dotted lines. As the controller, the controller A1704 is used in FIG. 13A as an example, and the main body L2408 is used by being worn as shown in the FIG. 13A. The supporter 1201 only need to be made of an insulating material, for example, cloth such as cotton, or leather, rubber, silicon, or the like.

Figure 13B:
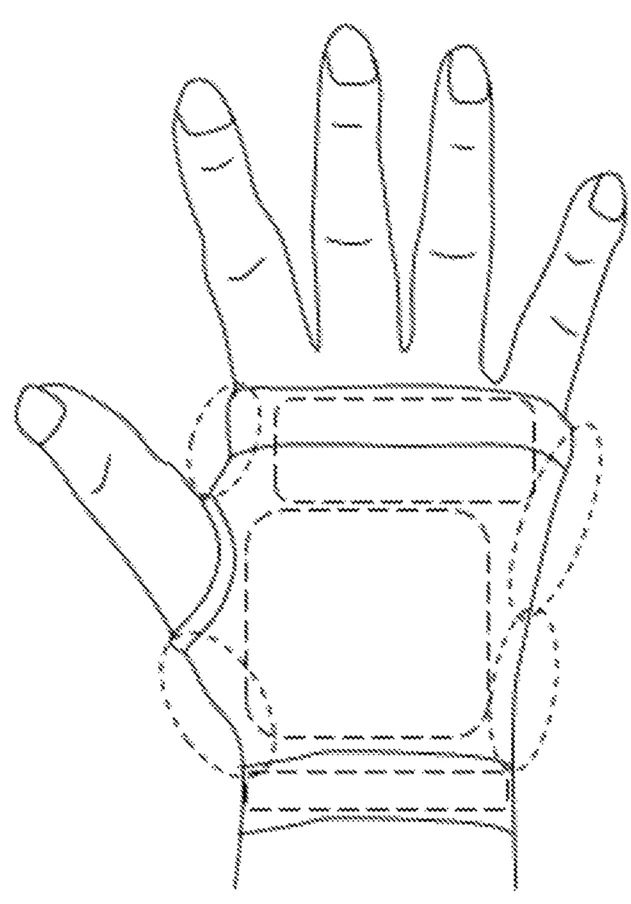
FIG. 13B is an explanatory view for explaining an electric signal for use in the current stimulation apparatus of the present invention.
Figure 13C:
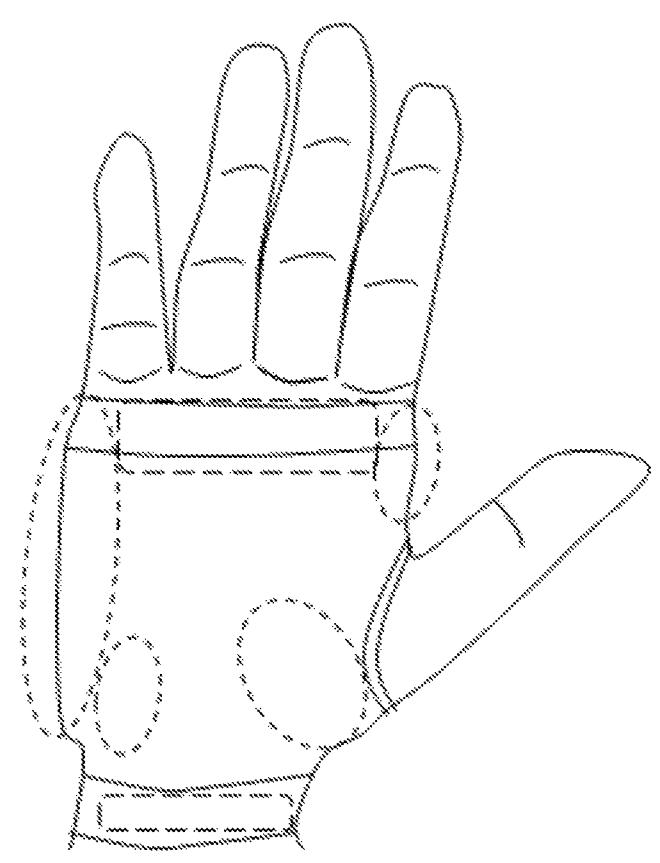
FIG. 13C is an explanatory view for explaining an electric signal for use in the current stimulation apparatus of the present invention.

Although the electrode E1202 and the electrode F1203 are arranged as shown in FIG. 13A, the present invention is not limited to this example. As the position where the electrodes are arranged, a plurality of regions surrounded by the dotted lines in FIGS. 13A to 13C are desirable because the electrodes can be contacted with the skin without fail. Hereinafter, each of the regions desirable for arranging these electrodes is referred to as an electrode region. Two electrode regions are selected from these electrode regions, and one electrode is disposed or two electrodes are disposed in each of these electrode regions. For example, electrodes may be arranged at the position of the base of the thumb and at a position between the wrist and the base of the little finger, respectively. FIG. 13B shows the electrode regions on the back side of the hand, and FIG. 13C shows the electrode regions on the palm side of the hand.

Figure 14:
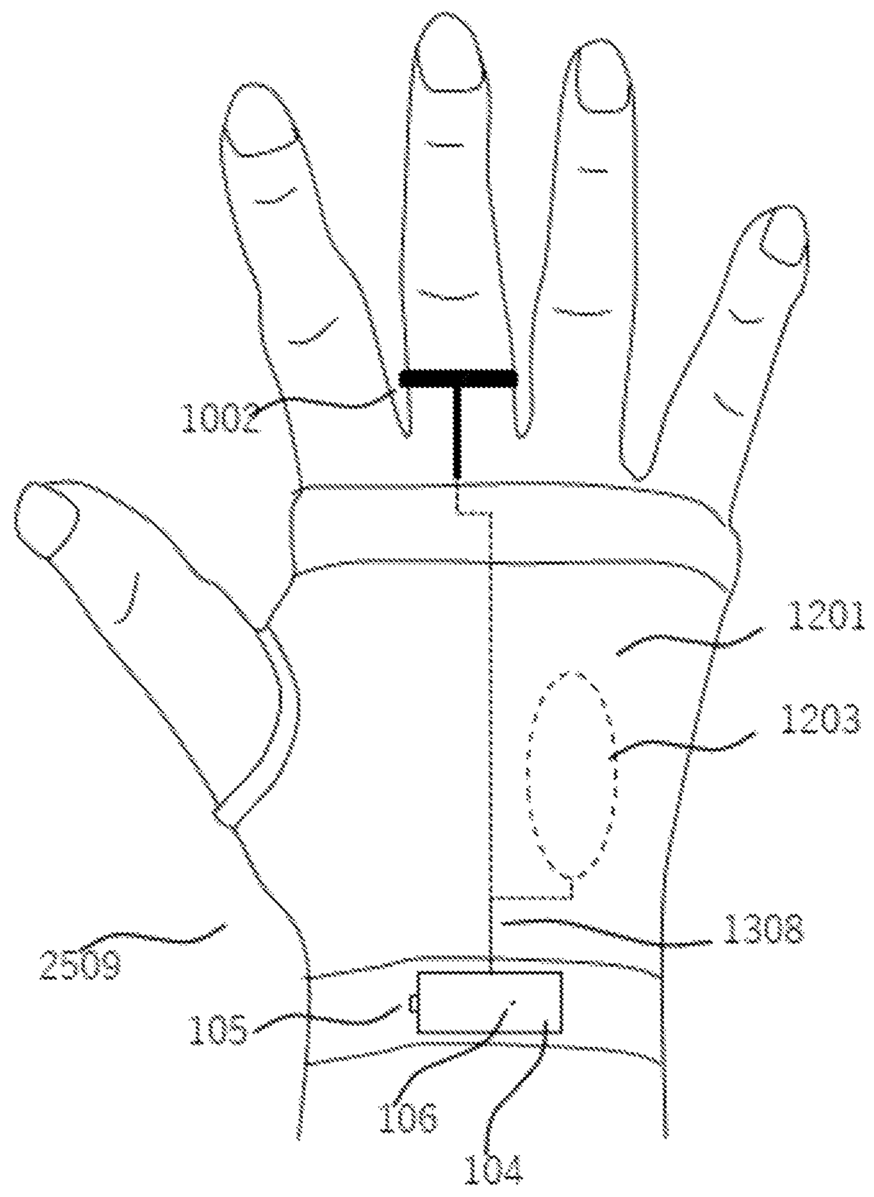
FIG. 14 is an explanatory view for explaining an electric signal for use in the current stimulation apparatus of the present invention.

FIG. 14 shows another modification. Although FIG. 13A shows a configuration in which the electrodes are arranged on the supporter 1201, the present invention is not limited to this, and a main body M2509 which uses the ring J1001 or the ring K1002 as one of the electrodes, may be used in the present invention. FIG. 14 shows a case in which the ring K1002 is used instead of the electrode E1202 in FIG. 13A, but the ring K1002 may be used instead of the electrode F1203.

Figure 15:
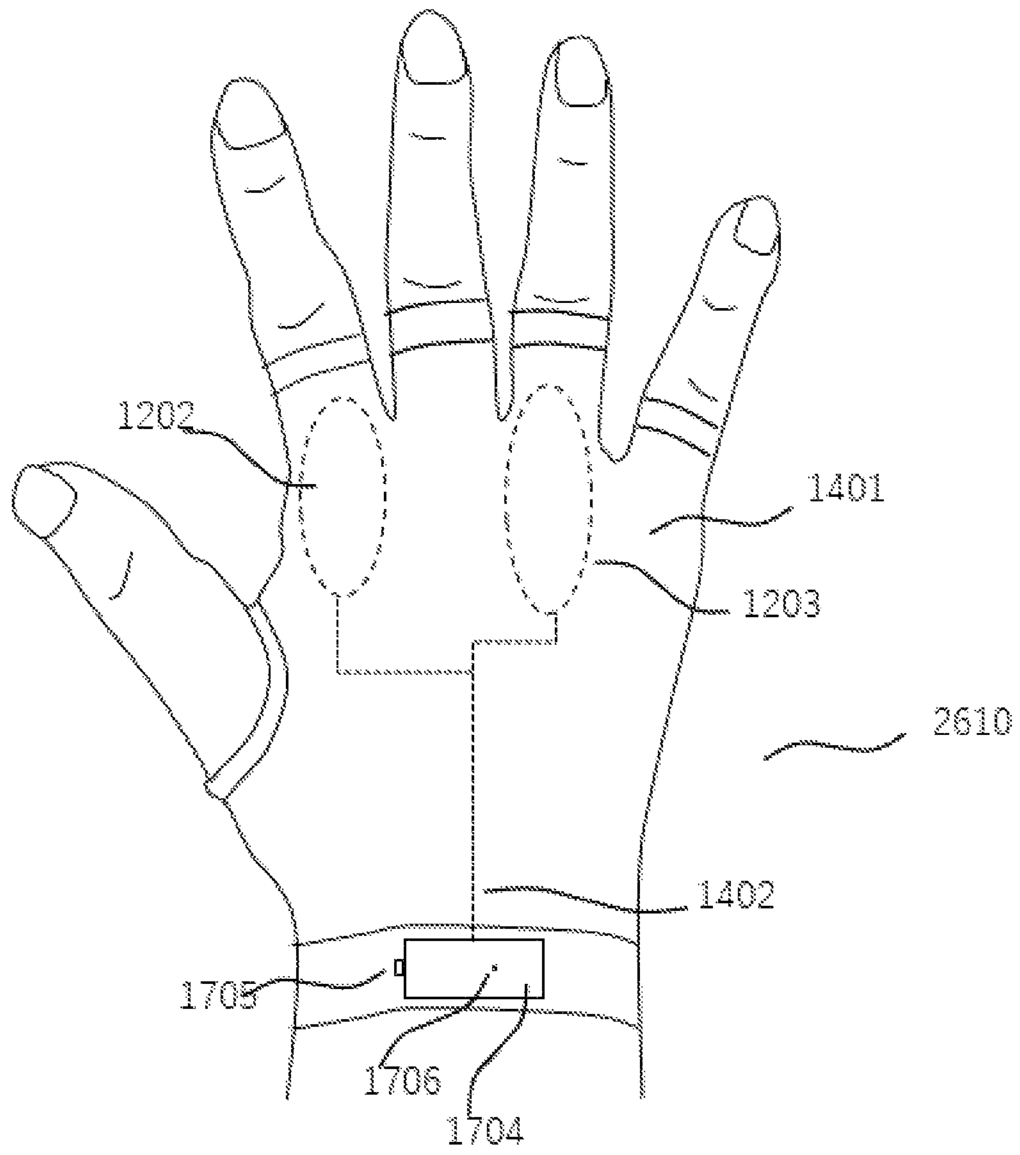
FIG. 15 is an explanatory view for explaining an electric signal for use in the current stimulation apparatus of the present invention.

FIG. 15 shows another modification. Although FIG. 14 and FIG. 13A and others show examples of supporter shapes used for wrists, the present invention is not limited to this, and FIG. 15 shows a main body N2610 in the shape of a glove. The main body N2610 has a glove 1401, the electrode E1202 and the electrode F1203 corresponding to the electrode A1702 and the electrode B1703 are arranged, and the electrode E1202 and the electrode F1203 are connected to the controller via a harness M1402. In FIG. 15, a controller A1704 is used. A glove 1401 only need to be made of an insulating material just as the supporter 1201, and may be made of cloth such as cotton, or leather, rubber, silicon, or the like. When a main body in the shape of a glove as shown in FIG. 15 is used, in the electrode regions shown in FIG. 13B and FIG. 13C, electrodes can be arranged on each finger and the surface of each finger covered with the gloves, and the ring A2101, the ring J1001, and the ring K1002, in the shape of a ring, are not required so that the mounting of the electrodes is simplified.

Unlike the above-described embodiments and modifications, the electrodes and the main bodies are not necessarily disposed to the distal portion of the limbs or to the vicinity thereof, but may be arranged in a device in contact with the distal portion of human body or to the vicinity thereof. The electrodes and the main bodies may be arranged, for example, on a keyboard or a mouse when using a personal computer, on a handle bar, an accelerator or a brake when driving a motorcycle or an bicycle, or on a pen a smartphone, or the like.

Figure 16A:
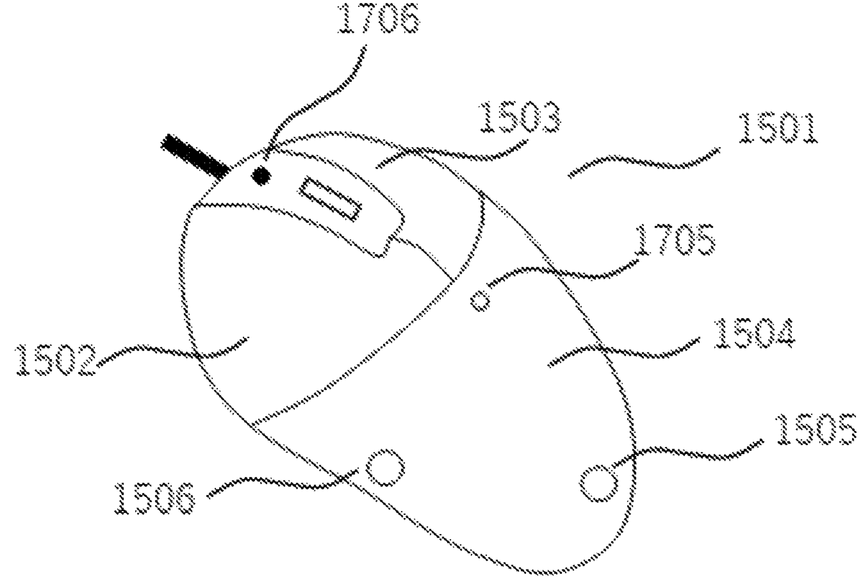
FIG. 16A is an explanatory view for explaining an electric signal for use in the current stimulation apparatus of the present invention.

FIG. 16A to 16D show examples thereof. FIG. 16A shows a case in which the electrodes and the main bodies are used in a mouse. A mouse 1501 may have a left click 1502, a right click 1503, and a body portion 1504 in contact with the palm of the hand, and may have an electrode G1505 and an electrode H1506 in the body portion 1504. As a controller, a controller A1704 may be disposed in the body portion 1504 and connected to the electrode G1505 or the electrode H1506. As for the arrangement of the electrodes, the electrodes may be arranged at the part where the thumb touches and at the proximal end of the body portion 1504, which is a position where the part close to the wrist of the palm side contacts, as shown in FIG. 16A. The electrode G1505 may be arranged on the right side surface of the body portion 1504, which is a position where the little finger contacts, in order that the current may flow to the thumb and the little finger by the electrode H1506 arranged on the thumb side and the electrode G1505. Alternatively, the electrode G1505 and the electrode H1506 may be disposed at the proximal end of the body portion 1504

Alternatively, the left click 1502 or the right click 1503 may be made of a conductive member instead of the electrode G1505, or the electrode G1505 may be arranged on the left click 1502 or the right click 1503 so that current flow between the thumb and the index finger or the middle finger. The electric signal may be supplied to the palm of the hand and a finger by the left click 1502 or the right click 1503 and the electrode H1506 disposed on the body portion 1504. An electrode H1506 may be arranged on the left click 1502; a conductor may be used at least on the surface of the left click 1502, and the electrode G1505 may be arranged on the right click 1503; or a conductor may be used at least on a surface of the right click 1503, so that current flows between the index finger and the middle finger. Further, a switch A1705 and an LED-A1706 may be arranged as shown in, for example, FIG. 16A.

Figure 16B:
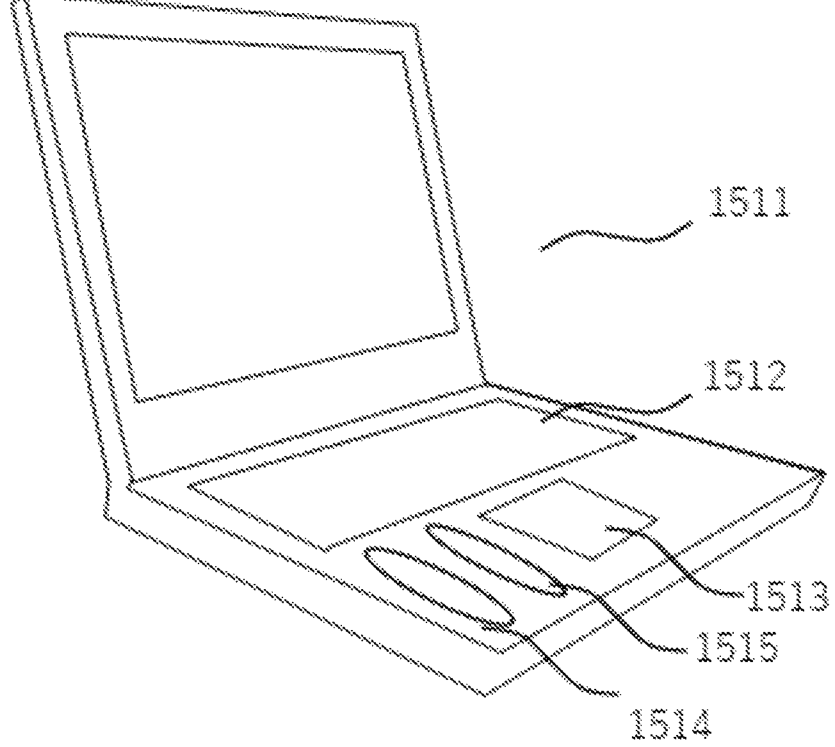
FIG. 16B is an explanatory view for explaining an electric signal for use in the current stimulation apparatus of the present invention.

FIG. 16B shows an example in which the present invention is applied to a laptop computer. As shown in FIG. 16B, a personal computer 1511 has an electrode J1514 and an electrode K1515 on the left side of a touch pad area 1513 in front of a keyboard area 1512, the touch pad area 1513 being used to operate the mouse pointer. The electrode J1514 and the electrode K1515 are connected to a controller disposed in the personal computer 1511. The controller may be any of the controllers described above. In FIG. 16B, the electrodes are disposed on the left side of the touch pad area 1513, but the present invention is not limited this, and the electrodes may be disposed on the right side, or may be disposed on both sides of the touch pad area 1513 to provide the above-described electric signals to each of the palms of both hands. The electric signals supplied through the electrode J1514 and the electrode K1515 may be controlled by an application installed in the personal computer 1511.

Figure 16C:
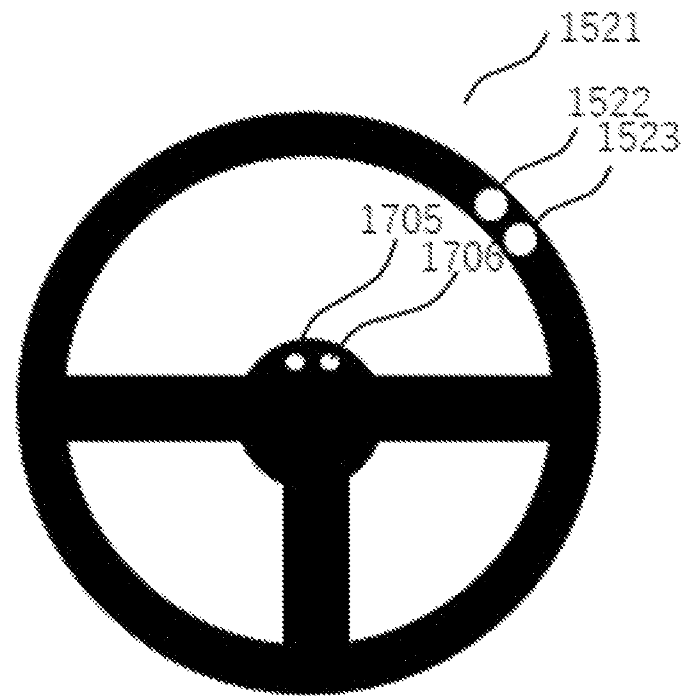
FIG. 16C is an explanatory view for explaining an electric signal for use in the current stimulation apparatus of the present invention.

FIG. 16C shows an example in which the present invention is applied to a steering wheel of a vehicle. An electrode L1522 and an electrode M1523 are disposed on a steering wheel 1521 as shown in FIG. 16C, and are connected to a controller disposed inside the steering wheel 1521. Further, the switch A1705 and the LED-A1706 may be arranged, for example, as shown in FIG. 16C. The controller may be any of the controllers described above. Although the electrode L1522 and the electrode M1523 are disposed on the right side of the steering wheel, the present invention is not limited thereto, and these electrodes may be disposed on the left side or on both sides of the steering wheel. In addition, although the electrode L1522 and the electrode M1523 are disposed on the front of the steering wheel, the present invention is not limited to this, and these electrodes may be disposed on side surface(s) of the steering wheel, or either electrode may be disposed on the front, and another on a side surface. In addition, the present invention may be applied by disposing the electrode L1522 and electrode M1523 on handle bars of motorcycles or bicycles, and not on a steering wheel of a vehicle.

Figure 16D:
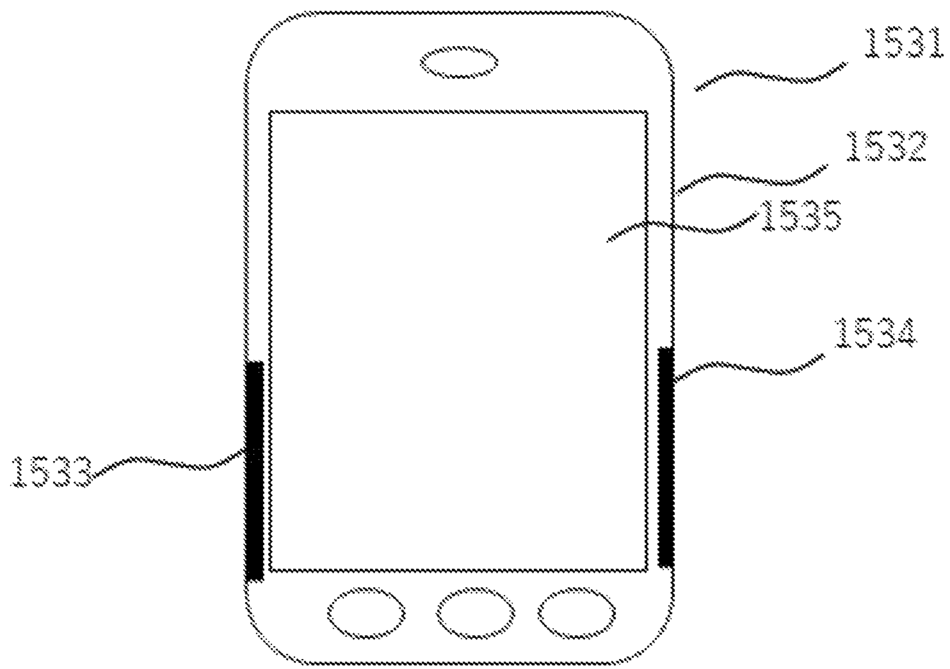
FIG. 16D is an explanatory view for explaining an electric signal for use in the current stimulation apparatus of the present invention.

FIG. 16D shows an embodiment in which the present invention is applied to a portable terminal. As shown in FIG. 16D, an electrode P1533 and an electrode Q1534 are disposed on the both sides of a chassis 1532 or a display portion 1535 of a smartphone 1531, and are connected to a controller disposed in the chassis 1532. The controller may be any of the above-mentioned controllers, and for example, the controller A1704 may be disposed in the chassis 1532 and may be connected to the electrode P1533 and the electrode Q1534. Although the electrode P1533 and the electrode Q1534 are disposed on the lower half of both sides of the chassis 1532, the present invention is not limited thereto, and these electrodes may be disposed on the upper half, or on the upper and lower side of one of the right side and the left side. The electric signals supplied via the electrode P1533 and the electrode Q1534 may be controlled by an application installed in the smartphone 1531.

In the examples of FIG. 16A to 16D, each of the controller and the electrode may be disposed as a separated body. For example, in the case of a mouse, a controller may be disposed in a personal computer to which the mouse is connected, and an application installed in the personal computer may be used to control an electric signal supplied to the limbs or to the vicinity thereof, via the electrodes. In the case of the steering wheel, the controller may be disposed not on the steering wheel but on, for example, an instrument panel or the like, and for example, a user interface of a car navigation system or the like may be used to control an electric signal to be supplied to the human body. Alternatively, controllers may be disposed on a mouse or a steering wheel, but the control such as the start or stop of the output may be controlled using a user interface of a personal computer or a car navigation system.

In each of FIGS. 7A to 16D described above, since a feeble and unfelt current is used as an electric signal to be supplied, the feeble and unfelt current does not give the user pain or discomfort, and the user does not even feel that the current is supplied, so that even while, for example, driving, doing office work, doing computer work such as typing or mouse operation, or fine hand working or the like (hereinafter collectively referred to simply as "operation"), the user is not affected at all by the electric signal supplied, and the user can easily and effortlessly continue these operations without any stress attributed to the electric signal while being supplied the electric signal. Further, during these operations, since the user can continue these operations while balancing the autonomic nerve at all times by using the electric signal of the present invention, it is possible to not only improve the operation efficiency but also to continue the safe operation. For example, when driving for a long time or at night, it is possible to drive while balancing the autonomic nerves at all times by using the electric signal of the present invention, so that the user feels no sleepiness and can prevent drowsy driving by preventing the parasympathetic nerves from becoming dominant, and it is possible to continue safe driving. Even when the personal computer is used for a long time or at night, it is possible to use the personal computer while balancing the autonomic nerves at all times by using the electric signal of the present invention, so that the user feels no sleepiness and improve concentration by preventing the parasympathetic nerves from becoming dominant, and it is possible to carry out the operation without mistakes continuously. In addition, secondary effects such as increased concentration can be expected due to the autonomic nervous system balanced, and thus it is desirable to use the electric signal of the present invention in office work, manual work, or driving.

In each of the above-described embodiments and various modifications, the pulse group using the rectangular wave is used as the electric signal to be used, but the present invention is not limited thereto. For example, the triangle wave may be used instead of the rectangular wave. Alternatively, the impulse train using a plurality of impulses may be used, or the sine waves may be used instead of the pulse group. Further, the electric signal having a positive and negative amplitude, or the unipolar waveform having only positive amplitude or negative amplitude may be used. The electric signal in the present invention is not limited to electric signals whose positive amplitude is equal to negative amplitude, and the electric signal whose positive amplitude is not equal to negative amplitudes, or the electric signal having different waveform for positive and negative waveforms, or the electric signal which has offset waveform may be used.

As the fifth signal frequency in the present invention, 5 Hz is used, but the present invention is not limited thereto. As the electric signal that can be expected to improve the balance of the autonomic nerve, for example, a DC may be desired. However, in the case of the DC continuing to flow, current tends to concentrate by a decrease of the conductivity on the contact surface between the skin and the electrode for example when the electrode used deteriorates or when dirt, dust, or impurities are generated or adhered, and during DC usage, current concentration tends to be kept at same position for a long time. In addition, the current concentration for a long time is not desirable because it can cause troubles such as burn injury, change of color or blister and the like on the skin even when the feeble current whose value is as weak as 300 μA is used. Therefore, in this modification, by applying an electric signal having an AC component instead of the DC, it is possible to avoid the occurrence of current concentration, and it is possible to avoid or mitigate continuation of the current concentration at the same position even if the current concentration occurs, so that it is possible to avoid troubles due to the current concentration.

It does not mean that any AC component which is not DC, i.e., which is not 0 Hz, will do. For example, about 0.1 Hz is not desired because it tends to substantially act as DC so that 0.5 Hz or more is desirable and 1 Hz or more is ideal. After all, as the ultra-low frequency, it seems that 1 Hz or more and 8 Hz or less seems most desirable, and in this embodiment, 5 Hz is used as the ultra-low frequency.

On the other hand, when the frequency of the AC component is high, the electric signal can produce an effect similar to that of DC. For example, in the case where the electric signal as in the present invention is applied, the effect equivalent to that of the DC can be obtained when the frequency is about 100 Hz, so that such a relatively high frequency, e.g., 300 Hz, can be used.

Although, in all of the above examples, the present invention is applied to a human body, the present invention is applicable to other living bodies other than a human body (hereinafter, simply referred to as living bodies). Examples of living bodies are living bodies kept in zoos such as lions and giraffes, or living bodies kept in the general household as pets such as dogs and cats, and domestic animals such as cattle, horses, pigs, chickens, goats and sheep, to which the present invention is applicable. Here, an example regarding the domestic animal is explained. Domestic animals are often housed in relatively small areas, for example cattle barns for the cattle, and autonomic balancing may be disrupted by lack of exercise, by confinement in small areas, or by stress from other factors. If these continue for a long time, growth, health, milk quality and quantity for cattle, and meat quality for beef cattle are greatly affected.

Therefore, by using the apparatus to which the present invention is applied, for the living body, for example, cattle, it is possible to improve the milk quality and the meat quality by balancing the autonomic nerves to reduce the stress. The apparatus used in this case can be the above-described main body A, this modification, or the like. However, it is required to resize the belt part A1701 or change the material to increase the strength thereof so as to apply to the foot of cattle, for example.

Because the main bodies as described above do not require a particularly large circuit configuration or battery, the living bodies do not feel stress related to the size or weight of the main bodies. Additional stress caused by the main bodies attached resolves immediately, and the above-mentioned unfelt output cannot be sensed by the living bodies, either, so that the living bodies are not conscious that the electric stimulation is given and do not feel any additional stress attributed to usage of the apparatus to which the present invention is applied. However, it is possible that the living bodies may be curious and lick or bite the attached unfamiliar apparatus, thereby to unintentionally push or destroy the switches. To prevent such incidents, some device is considered necessary to cover the switches and to increase the strength of the controller and the belt section. A configuration in which the switch is eliminated from the main body and to be remote controlled by radio from the outside is more preferable because unintentional operations of the switches and damages to the switches due to being licked or bitten by the living bodies can be avoided.

When the apparatus of the present invention is used for the living bodies, the electrode to be used, for example, the electrode A1702 or the electrode B1703 described above, is not suitable for use as it is, in some cases. Limbs of the living bodies are usually covered with skin hair, so that the current is not adequately supplied to limbs. Therefore, it is preferable that the electrode A1702 and the electrode B1703 are made of elastic materials having high elasticity, such as conductive rubbers or conductive fibers, instead of conductive resins or metals, so that the current from the electrodes is sufficiently supplied to the limbs. Alternatively, the surface of the electrode A1702 or electrode B1703 may be coated with a highly viscous conductive gel so that a sufficient current can be supplied to the limb of the living bodies.

By using the apparatus of the present invention for the living bodies, the following effects can be expected. Each of the following effects can be expected not only independently but also simultaneously as a plurality of effects. One of the effects is the suppression of excessive sympathetic nerve tone. The reason why the sympathetic nerve becomes dominant is not limited to a specific reason, and for example, stress from confinement in a small pen or in a small room can be cited. Other reasons include stress of weather, such as unusual low and high temperatures, typhoons, strong winds, prolonged rain and drying, by caution caused by construction work carried out in the neighborhood, or a change in physical condition such as poor health condition, pregnancy, or the like. Conversely, the reason why the parasympathetic nervous system becomes dominant is insufficient sleep, fatigue, or aging. Other reasons for the imbalance of the autonomic nervous system include the presence or absence of a meal, seasons or turns of seasons, visceral diseases, or injuries, etc.

Against the above-mentioned imbalance of the autonomic nervous system, by supplying the above-mentioned electric signals to the limbs by using the present invention, the autonomic nervous system is balanced, the living bodies are released from the stress, and the function against the injury or disease of the living bodies is maintained in a healthy state, so that the present invention can be used to maintain and manage the physical conditions of the living bodies including health conditions improvement and maintenance, as well as improving allergic symptoms and accelerating the healing of the injury or disease as secondary effects, by releasing from the stress and improving the physical condition, are also expected.

Other effects can be expected by using the apparatus of the present invention for living bodies. Here, other effects means control of activities. For example, in the case of living bodies of elderlies, because activity in itself declines and the parasympathetic nerve tends to be dominant, which would cause lack of exercise, muscle weakness, joint damage and visceral disease resulting from lack of exercise. Therefore, as described above, by supplying the electric signal of the present invention to the distal portion of the limbs of the living bodies or to the vicinity thereof with a main body to which the present invention is applied or a device having a function capable of outputting pulses equivalent thereto, it is possible to prevent the parasympathetic nerve from becoming dominant more than necessary, and to prevent activities or liveness of the living bodies so that it is usable to eliminate lack of exercise and to keep and manage the physical condition of the living bodies. On the contrary, for the living bodies whose sympathetic nerve is dominant more than necessary, by supplying the electric signal of the present invention to the distal portion of the limbs or to the vicinity thereof, it is possible to prevent the sympathetic nerve from becoming dominant more than necessary, to resolve the insomnia disorder or insufficient sleep thereby to release the stress due to the sleep disorder, and thus the present invention can be used for keeping and managing the physical condition of the living bodies. The aforementioned effects can be expected for the human body as well.

By the apparatus of the present invention, it is possible not only to perform health management of the living bodies but also to control quality in the case of domestic animals. For example, for beef cattle whose parasympathetic nerves tends to become excessively dominant, the apparatus of the present invention is used to balance the autonomic nerves, to prevent the parasympathetic nerves from becoming excessively dominant thereby to enhance (returning to normal) the sympathetic nerve function, and to increase the activity of beef cattle, so that it is possible to prevent the so-called lean rate from decreasing. As to beef cattle whose sympathetic nerves tends to become excessively dominant, the present invention is used to prevent the sympathetic nerves from becoming excessively dominant thereby to enhance (returning to normal) the parasympathetic nerve function, and to limit the activity of beef cattle, so that it is possible to control meat quality by regulating meat hardness and lipids, and also to control, for example, to prevent the rate of the so-called marbling and soft meat from decreasing. In this case, neither the movement of the domestic animals is forcibly restricted nor the movement is forced, so that the domestic animals are not stressed at all.

Figure 17:
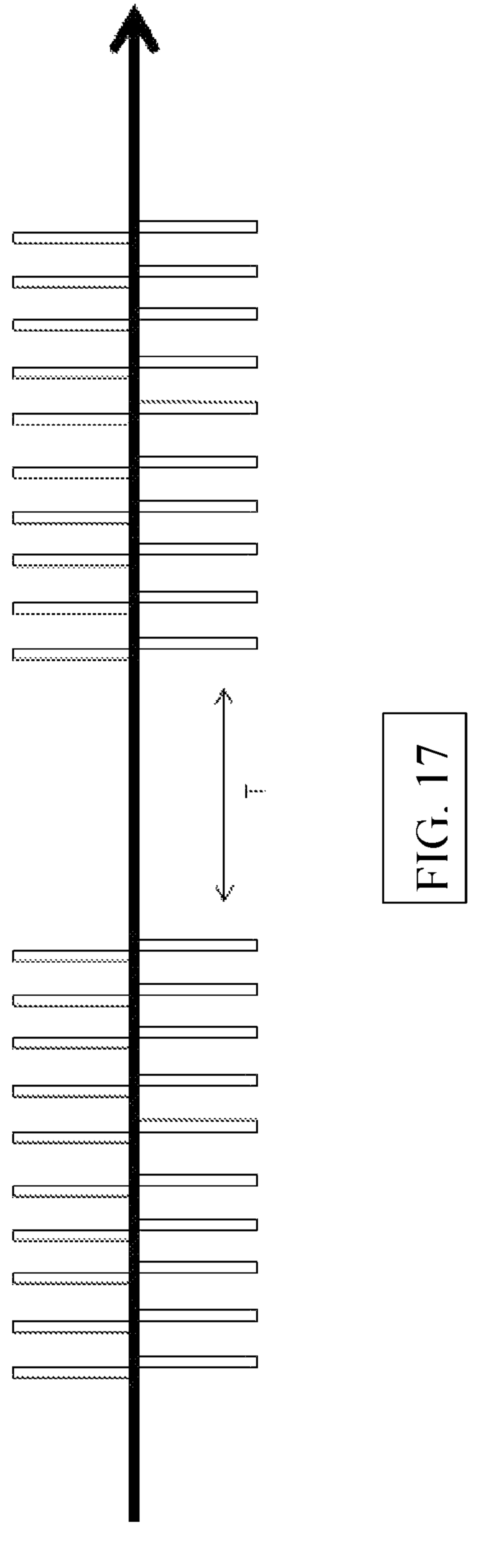
FIG. 17 is an explanatory view for explaining an electric signal for use in the current stimulation apparatus of the present invention.

In the above, the case of using the unfelt output and the very weak felt output (hereinafter collectively referred to as "weak current") in a treatment method using the electric signals of FIGS. 3A and 3B to the distal portion of the limbs or to the vicinity thereof is described; however this does not mean that only a weak current is effective in this treatment method. For example, the same effects can be obtained by attaching the electrode pad A111 and the electrode pad B112 to the distal portion of the limbs or to the vicinity thereof such as the wrist using the current stimulation apparatus 1 in FIG. 1, and by supplying a current of, for example, about several mA to 20 mA. In this case, because the current stimulation apparatus 1 is large and the electric signal of a relatively large amplitude is supplied to the wrist or the like, the patient has to use the apparatus while sitting on the chair relaxedly or lie on the bed rather than receiving treatment during work or the like. The current stimulation apparatus 1 of FIG. 1 may be to output a weak current, that is, the waveform generator section 204 may also output a weak current. In the above-mentioned methods, in which a weak current is used in the distal portion of the limbs or to the vicinity thereof, an electric signal as shown in FIG. 17 can also be used instead of the electric signal as shown in FIGS. 3A and 3B. As an example of parameter to be used, an electric signal having a frequency of 5 Hz or 300 Hz, a pulse width of 50 msec, and an amplitude of 50 μA or 300 μA may be repeatedly output for, for example, 1 second, at intervals of a predetermined constant time T, for example, 2 seconds, as described above.

This international application claims priority from Japanese Patent Application No. 2019-34960 filed on Feb. 27, 2019 and Japanese Patent Application No. 2019-230731 filed on Dec. 20, 2019, and the entire contents of Japanese Patent Application No. 2019-34960 and 2019-230731 are incorporated herein by reference.

DESCRIPTION OF REFERENCES

1 Current stimulation apparatus
11 Main body section
12 Stop switch
14 Connector section
15 Main power
16 Code
17 Controller
18 Encoder
105 Switch
111 Electrode pad A
112 Electrode pad B
114 Display section
201 User IF section
203 Control section
204 Waveform generator section
205 Memory
206 Power supply section
207 Timer
208 Terminal A
209 Terminal B
301 The first electric signal
302 The second electric signal
303 Third electric signal
304 The fourth electric signal
305 Fifth electric signal
1001 Ring J
1002 Ring K
1006 Connector J
1007 Cable J
1008 Harness E
1107 Cable K
1201 Supporter
1202 Electrode E
1203 Electrode F
1208 Harness F
1401 Glove
1402 Harness M
1501 Mouse
1502 Left click
1503 Right click
1504 Body portion
1505 Electrode G
1506 Electrode H
1511 Personal computer
1512 Keyboard area
1513 Touch pad area
1514 Electrode J
1515 Electrode k
1521 Steering wheel
1522 Electrode L
1523 Electrode M
1531 Smartphone
1532 Chassis
1533 Electrode P
1534 Electrode Q
1535 Display portion
1700 Main body A
1701 Belt part A
1702 Electrode A
1703 Electrode B
1704 Controller A
1705 Switch A
1706 LED-A
1707 Elastic part A
1708 Harness A
1773 Battery
1803 Main body C
1900 Cable M
1901 Mounting part
1902 Terminal part A
1903 Terminal part B
1904 Main Body D
1905 Controller D
1906 Switch B
1907 LED-B
1908 Connector K
1909 Harness B
2100 Main body H
2101 Ring A
2102 Electrode C
2103 Electrode D
2104 terminal part C
2105 terminal part D
2106 connector H
2107 Cable H
2108 Harness C
2109 Harness D
2110 Bracelet
2206 Main body J
2307 Main body K
2408 Main body L
2509 Main body M
2610 Main body N

The invention claimed is:

1. A current stimulation apparatus comprising:

a controller including a waveform generator, a control section and a power supply section, wherein the waveform generator is configured to output an electric signal during a treatment time, the control section is configured to control the waveform generator, and the power supply section is configured to supply electric power to the waveform generator and the control section; and a set of electrodes to provide the output electric signal, wherein the controller is configured to output the electrical signal, the electric signal is a repetitive output of a fifth electric signal, the fifth electric signal including:

a first electric signal being a first pulse train and having an amplitude increasing from a first amplitude, the first amplitude being not zero;

a second electric signal being a second pulse train and having a second amplitude and being output after the first electric signal;

a third electric signal being a third pulse train and having a decreasing amplitude and being output after the second electric signal; and a fourth electric signal being a fourth pulse train and having a fourth amplitude, the fourth amplitude being not zero, wherein the fourth amplitude is automatically changed in the case that the second amplitude is changed, the second amplitude and the fourth amplitude do not fall below or exceed a certain value in the case that the second amplitude is changed, each pulse in each of the first pulse train, the second pulse train, the third pulse train and the fourth pulse train has a common frequency during the treatment time, the first electric signal has a first duration of a plurality of first durations, the second electric signal has a second duration of a plurality of second durations, the third electric signal has a third duration of a plurality of third durations, the fourth electric signal has a fourth duration of a plurality of fourth durations, the fifth electric signal has a fifth duration of a plurality of fifth durations, and the fifth duration being equal to a sum of the first duration of the plurality of first durations, the second duration of the plurality of second durations, the third duration of the plurality of third durations and the fourth duration of the plurality of fourth durations, the fifth duration being a sequence in an order of the first duration of the plurality of first durations, the second duration of the plurality of second durations, the third duration of the plurality of third durations and the fourth duration of the plurality of fourth durations, and at least one of the first duration, the second duration, the third duration and the fourth duration is proportionally controlled to become shorter or longer independently of the treatment time in the case that the fifth duration is changed by a variable control prior to beginning the treatment time or prior to the start of the treatment time.

2. The current stimulation apparatus according to claim 1, wherein the fourth amplitude is changed in the case that the second amplitude is changed by the variable control.

* * * * *